US008592627B2

(12) United States Patent
Sugimoto

(10) Patent No.: US 8,592,627 B2
(45) Date of Patent: Nov. 26, 2013

(54) PROCESS FOR PRODUCING (METH)ACRYLIC ACID AND CRYSTALLIZATION SYSTEM

(75) Inventor: Takashi Sugimoto, Himeji (JP)

(73) Assignee: Nippon Shokubai Co., Ltd., Osaka (JP)

(*) Notice: Subject to any disclaimer, the term of this patent is extended or adjusted under 35 U.S.C. 154(b) by 102 days.

(21) Appl. No.: 13/266,983

(22) PCT Filed: May 7, 2010

(86) PCT No.: PCT/JP2010/057808
§ 371 (c)(1),
(2), (4) Date: Oct. 28, 2011

(87) PCT Pub. No.: WO2010/131603
PCT Pub. Date: Nov. 18, 2010

(65) Prior Publication Data
US 2012/0046432 A1 Feb. 23, 2012

(30) Foreign Application Priority Data

May 15, 2009 (JP) .................. 2009-119162
May 15, 2009 (JP) .................. 2009-119163

(51) Int. Cl.
C07C 51/43 (2006.01)

(52) U.S. Cl.
USPC ........................................ 562/600

(58) Field of Classification Search
USPC ................................ 562/600, 608
See application file for complete search history.

(56) References Cited

U.S. PATENT DOCUMENTS

| 4,893,999 A | 1/1990 | Chmelir et al. |
| 4,920,202 A | 4/1990 | Irie et al. |
| 5,264,495 A | 11/1993 | Irie et al. |
| 5,275,773 A | 1/1994 | Irie et al. |
| 5,385,983 A | 1/1995 | Graham |
| 5,409,771 A | 4/1995 | Dahmen et al. |
| 5,462,972 A | 10/1995 | Smith et al. |
| 5,546,763 A | 8/1996 | Kikuchi et al. |
| 5,597,873 A | 1/1997 | Chambers et al. |
| 5,610,220 A | 3/1997 | Klimmek et al. |
| 5,633,316 A | 5/1997 | Gartner et al. |
| 5,669,894 A | 9/1997 | Goldman et al. |
| 5,674,633 A | 10/1997 | Saunders et al. |
| 5,756,602 A | 5/1998 | Hui et al. |
| 6,164,455 A | 12/2000 | Kakita et al. |
| 6,207,796 B1 | 3/2001 | Dairoku et al. |
| 6,241,928 B1 | 6/2001 | Hatsuda et al. |
| 6,291,636 B1 | 9/2001 | Miyake et al. |
| 6,472,478 B1 | 10/2002 | Funk et al. |
| 6,503,979 B1 | 1/2003 | Funk et al. |
| 6,710,141 B1 | 3/2004 | Heide et al. |
| 6,867,269 B2 | 3/2005 | Sakamoto et al. |
| 6,875,511 B2 | 4/2005 | Dairoku et al. |
| 6,906,159 B2 | 6/2005 | Dairoku et al. |
| 6,987,151 B2 | 1/2006 | Gartner et al. |
| 7,091,253 B2 | 8/2006 | Dairoku et al. |
| 7,714,164 B2 | 5/2010 | Nakagawa |
| 7,732,635 B2 | 6/2010 | Matsumoto |
| 2004/0110897 A1 | 6/2004 | Sakamoto et al. |
| 2004/0186229 A1 | 9/2004 | Heide et al. |
| 2005/0215734 A1 | 9/2005 | Dairoku et al. |
| 2005/0221457 A1 | 10/2005 | Tsobanakis et al. |
| 2007/0129572 A1 | 6/2007 | Shibusawa et al. |
| 2007/0238898 A1 | 10/2007 | Matsumoto |
| 2008/0004408 A1 | 1/2008 | Stueven et al. |
| 2008/0071111 A1 | 3/2008 | Nakagawa |
| 2009/0188270 A1 | 7/2009 | Takahashi et al. |
| 2009/0298144 A1 | 12/2009 | Tsobanakis et al. |
| 2010/0069583 A1 | 3/2010 | Kasuga et al. |

FOREIGN PATENT DOCUMENTS

| CA | 2 319 786 | 2/1999 |
| CN | 1104927 | 7/1995 |
| CN | 1134942 | 11/1996 |
| CN | 1314422 | 9/2001 |
| EP | 0 349 240 | 1/1990 |
| EP | 0 450 923 | 10/1991 |
| EP | 0 450 924 | 10/1991 |
| EP | 0 605 150 | 7/1994 |
| EP | 0 668 080 | 8/1995 |
| EP | 0 812 873 | 12/1997 |
| JP | 6-159831 | 6/1994 |
| JP | 7-224304 | 8/1995 |
| JP | 7-242709 | 9/1995 |
| JP | 8-259606 | 10/1996 |
| JP | 2005-521718 | 7/2005 |
| JP | 2005-207660 | 8/2005 |
| JP | 2007-182437 | 7/2007 |

(Continued)

OTHER PUBLICATIONS

International Search Report issued Jun. 1, 2010 in International (PCT) Application No. PCT/JP2010/057808 of which the present application is the national stage.
Office Action issued Jul. 26, 2013 in corresponding Chinese Application No. 201080018465.X, with English translation thereof.
Office Action issued Jun. 27, 2013 in Chinese Application No. 201080018295.5, with English translation thereof.

Primary Examiner — Brian J Davis
(74) Attorney, Agent, or Firm — Wenderoth, Lind & Ponack, L.L.P.

(57) ABSTRACT

A process for producing (meth)acrylic acid comprising the steps of: supplying a cooling medium to a crystallizer (1) from a heat source device (4A), thereby crystallizing (meth)acrylic acid from a crude (meth)acrylic acid solution; discharging the cooling medium from the crystallizer (1) and returning the cooling medium to the heat source device (4A); supplying a heating medium to the crystallizer (1) from a heat source device (4B), thereby melting the (meth)acrylic acid; and discharging the heating medium from the crystallizer (1) and returning the heating medium to the heat source device (4B); wherein temperature of the cooling medium returned to the heat source device (4A) is maintained constant by utilizing a first buffer tank (5); and temperature of the heating medium returned to the heat source device (4B) is maintained constant by utilizing a second buffer tank (6).

20 Claims, 9 Drawing Sheets

(56) References Cited

FOREIGN PATENT DOCUMENTS

| | | |
|---|---|---|
| JP | 2007-277182 | 10/2007 |
| JP | 2008-74759 | 4/2008 |
| JP | 2008-115103 | 5/2008 |
| WO | 99/42494 | 8/1999 |
| WO | 99/42496 | 8/1999 |
| WO | 99/43720 | 9/1999 |
| WO | 01/16346 | 3/2001 |
| WO | 01/38402 | 5/2001 |
| WO | 2005/016393 | 2/2005 |
| WO | 2005/095320 | 10/2005 |
| WO | 2006/034806 | 4/2006 |
| WO | 2006/087083 | 8/2006 |
| WO | 2006/087084 | 8/2006 |
| WO | 2007/106100 | 9/2007 |
| WO | 2008/027742 | 3/2008 |
| WO | 2008/114745 | 9/2008 |

PROCESS FOR PRODUCING (METH)ACRYLIC ACID AND CRYSTALLIZATION SYSTEM

TECHNICAL FIELD

The present invention relates to a process for producing (meth)acrylic acid comprising a crystallizing step and/or a melting step. The present invention also relates to a crystallization system.

BACKGROUND ART

Conventionally, a process for industrially producing (meth)acrylic acid by gas-phase catalytic oxidation of a (meth)acrylic acid production raw material has been known. A (meth)acrylic acid-containing gas produced by gas-phase catalytic oxidation of the (meth)acrylic acid production raw material is, for example, collected by a liquid medium to be recovered as a crude (meth)acrylic acid solution, and then, the crude (meth)acrylic acid solution is purified by methods such as distillation, diffusion, extraction, crystallization, or the like.

Patent Literature 1 discloses a method for purifying a crude (meth)acrylic acid solution by crystallization. In the case where a crude (meth)acrylic acid solution is purified by crystallization, cooling is needed for crystallizing (meth)acrylic acid from a crude (meth)acrylic acid solution, and heating is needed for obtaining purified (meth)acrylic acid by melting crystallized (meth)acrylic acid. However, Patent Literature 1 does not specifically describe a method for cooling and heating in the crystallization.

Patent Literature 2 discloses that cooling water generated by an absorption refrigerator is used in a crystallizing step when a crude (meth)acrylic acid solution is purified by crystallization. However, Patent Literature 2 does not describe techniques for stable operation of the refrigerator in the crystallization and reduction of consumption energy of the refrigerator used as a heat source device.

CITATION LIST

Patent Literature

PATENT LITERATURE 1
Japanese Unexamined Laid-open Patent Application Publication No. 2008-74759
PATENT LITERATURE 2
Japanese Unexamined Laid-open Patent Application Publication No. 2007-277182

SUMMARY OF INVENTION

Technical Problem

When a crude (meth)acrylic acid solution is cooled by a cooling medium to crystallize (meth)acrylic acid, temperature of the cooling medium discharged from a crystallizer tends to be high at the beginning and drop as the progress of crystallizing. Similarly, when crystallized (meth)acrylic acid is heated by a heating medium to be melted, temperature of the heating medium discharged from a crystallizer tends to be low at the beginning and rise as the progress of melting. Therefore, in the case where the temperature of the cooling medium or the heating medium discharged from the crystallizer is adjusted by a heat source device so that the cooling medium or the heating medium is supplied to the crystallizer again, cooling or heating load of the heat source device changes due to the temperature change of the cooling medium or the heating medium to be returned to the heat source device. As a result, operation of the heat source device is destabilized, thereby destabilizing the crystallization operation and increasing consumption energy of the heat source device.

The present invention has been achieved in view of the above circumstances, and the object of the present invention is to provide a process for producing (meth)acrylic acid that enables reducing the temperature change of a cooling medium or a heating medium returned to a heat source device from a crystallizer, thereby stabilizing the operation of the heat source device to stabilize crystallizing and melting operations, and reducing the consumption energy. The another object of the present invention is to provide a crystallization system that realizes stabilized crystallizing and melting operations by stabilizing the operation of a heat source device and reduction of the consumption energy.

Solution to Problem

A process for producing (meth)acrylic acid of the present invention which solves the above problems comprises the steps of: supplying a cooling medium to a crystallizer from a heat source device, thereby crystallizing (meth)acrylic acid from a crude (meth)acrylic acid solution; and discharging the cooling medium from the crystallizer and returning the cooling medium to the heat source device; wherein temperature of the cooling medium returned to the heat source device is maintained constant by a first adjustment operation or a second adjustment operation; the first adjustment operation is performed by feeding at least a part of the cooling medium to be returned to the heat source device from the crystallizer into an upper part of a first buffer tank and discharging the cooling medium from a lower part of the first buffer tank to return to the heat source device; and the second adjustment operation is performed by feeding at least a part of the cooling medium to be supplied to the crystallizer from the heat source device and/or the cooling medium to be returned to the heat source device from the crystallizer into the lower part of the first buffer tank and discharging the cooling medium from the upper part of the first buffer tank to return to the heat source device.

According to the above producing process, temperature of the cooling medium returned to the heat source device can be maintained constant by the first and second adjustment operations. Therefore, cooling load of the heat source device is easily maintained constant, and as a result, the heat source device can stably work, crystallizing operation can be stabilized, and hence, the consumption energy can be reduced.

An another process for producing (meth)acrylic acid of the present invention comprises the steps of: supplying a heating medium to a crystallizer from a heat source device, thereby melting crystallized (meth)acrylic acid; and discharging the heating medium from the crystallizer and returning the heating medium to the heat source device; wherein temperature of the heating medium returned to the heat source device is maintained constant by a third adjustment operation or a fourth adjustment operation; the third adjustment operation is performed by feeding at least a part of the heating medium to be returned to the heat source device from the crystallizer into an lower part of a second buffer tank and discharging the heating medium from an upper part of the second buffer tank to return to the heat source device; and the fourth adjustment operation is performed by feeding at least a part of the heating medium to be supplied to the crystallizer from the heat source device and/or the heating medium to be returned to the heat source device from the crystallizer into the upper part of the second buffer tank and discharging the heating medium from the lower part of the second buffer tank to return to the heat source device.

According to the above producing process, temperature of the heating medium returned to the heat source device can be maintained constant by the third and fourth adjustment operations. Therefore, heating load of the heat source device is easily maintained constant, and as a result, the heat source device can stably work, melting operation can be stabilized, and hence, the consumption energy can be reduced.

A still another process for producing (meth)acrylic acid of the present invention comprises the steps of: supplying a cooling medium to a crystallizer from a heat source device, thereby crystallizing (meth)acrylic acid from a crude (meth)acrylic acid solution; discharging the cooling medium from the crystallizer and returning the cooling medium to the heat source device; supplying a heating medium to the crystallizer from a heat source device, thereby melting the (meth)acrylic acid; and discharging the heating medium from the crystallizer and returning the heating medium to the heat source device; wherein temperature of the cooling medium returned to the heat source device is maintained constant by the said first adjustment operation or the said second adjustment operation; temperature of the heating medium returned to the heat source device is maintained constant by the said third adjustment operation or the said fourth adjustment operation. According to the above producing process, the heat source device can stably work both in the crystallizing step and the melting step, crystallizing operation and melting operation can be stabilized, and hence, the consumption energy can be reduced.

A still another process for producing (meth)acrylic acid of the present invention comprises the steps of: supplying a cooling medium to a first crystallizer from a heat source device, thereby crystallizing (meth)acrylic acid from a crude (meth)acrylic acid solution; discharging the cooling medium from the first crystallizer and returning the cooling medium to the heat source device; supplying a heating medium to a second crystallizer from the heat source device, thereby melting crystallized (meth)acrylic acid; and discharging the heating medium from the second crystallizer and returning the heating medium to the heat source device; wherein the heat source device is a refrigerator; temperature of the cooling medium returned to the heat source device is maintained constant by the said first adjustment operation or the said second adjustment operation; temperature of the heating medium returned to the heat source device is maintained constant by the said third adjustment operation or the said fourth adjustment operation. Here, in the first and second adjustment operations, the first crystallizer is used, and in the third and fourth adjustment operations, the second crystallizer is used. When a refrigerator is employed as the heat source device, it becomes possible to utilize both the cooling medium and the heating medium supplied from the refrigerator for the production of (meth)acrylic acid, and hence, consumption energy for the production of (meth)acrylic acid can be decreased, and efficient production of (meth)acrylic acid can be realized.

In the above embodiment where the first crystallizer and the second crystallizer are used, it is preferred that a part or all of the cooling medium discharged from the first crystallizer is utilized as a source of the heating medium, and a part or all of the heating medium discharged from the second crystallizer is utilized as a source of the cooling medium. In this case, the cooling medium having low temperature retained in the first buffer tank is not likely to be rapidly consumed by the first adjustment operation, and the heating medium having high temperature retained in the second buffer tank is not likely to be rapidly consumed by the third adjustment operation. Therefore, it becomes possible that the effects of the first and third adjustment operations are exerted for a longer period. In addition, the capacities of the buffer tanks are able to be lessened, thereby being able to reduce the construction cost. Further, operation of the heat source device (refrigerator) can be stabilized and the consumption energy of the heat source device (refrigerator) can be decreased.

Concerning a rule for utilizing the cooling medium and the heating medium as the mutual sources, it is preferred that the cooling medium discharged from the first crystallizer is utilized as the source of the heating medium when temperature of the cooling medium discharged from the first crystallizer is higher than that of the heating medium discharged from the second crystallizer; and the heating medium discharged from the second crystallizer is utilized as the source of the cooling medium when temperature of the heating medium discharged from the second crystallizer is lower than that of the cooling medium discharged from the first crystallizer.

Concerning the rule for utilizing the cooling medium and the heating medium as the mutual sources, it is also preferred that the cooling medium discharged from the first crystallizer is utilized as the source of the heating medium when temperature of the cooling medium discharged from the first crystallizer is higher than a predetermined temperature between temperature of the cooling medium supplied from the heat source device (refrigerator) and temperature of the heating medium supplied from the heat source device (refrigerator); and the heating medium discharged from the second crystallizer is utilized as the source of the cooling medium when temperature of the heating medium discharged from the second crystallizer is lower than the predetermined temperature between temperature of the cooling medium supplied from the heat source device (refrigerator) and temperature of the heating medium supplied from the heat source device (refrigerator).

In the process for producing (meth)acrylic acid of the present invention, it is preferred that the first buffer tank retains a certain amount of the cooling medium, the second buffer tank retains a certain amount of the heating medium, and each of the cooling medium retained in the first buffer tank and the heating medium retained in the second buffer tank has a temperature gradient such that an upper part is high-temperature and a lower part is low-temperature. Thereby, it becomes easy to maintain temperature of the cooling medium or the heating medium constant by the first to fourth adjustment operations.

Temperature of the cooling medium returned to the heat source device is preferably adjusted depending on temperatures of the upper part and the lower part of the cooling medium retained in the first buffer tank, and temperature of the heating medium returned to the heat source device is preferably adjusted depending on temperatures of the upper part and the lower part of the heating medium retained in the second buffer tank. By the above operations, a flow rate of discharging the cooling medium or the heating medium having high or low temperature from the buffer tank is adjusted, and hence, the effects of the first to fourth adjustment operations can be exerted for a longer period.

It is preferred that the first buffer tank is provided with openings at the upper part and the lower part thereof, through which the cooling medium passes, wherein distance between the opening at the upper part and the opening at the lower part of the first buffer tank is equal to or more than a maximum cross-section length of the first buffer tank, and the second buffer tank is provided with openings at the upper part and the lower part thereof, through which the heating medium passes, wherein distance between the opening at the upper part and the opening at the lower part of the second buffer tank is equal to or more than a maximum cross-section length of the second buffer tank. Thereby, the temperature gradient is easily generated in the cooling medium or the heating medium retained in the buffer tank in a vertical direction, and it becomes easy to maintain the temperature of the cooling medium or the heating medium returned to the heat source device constant.

The producing process of the present invention may further comprise the steps of: dehydrating glycerin or 2-methylglycerin to convert to (meth)acrolein; and oxidizing the (meth) acrolein to convert to (meth)acrylic acid, thereby obtaining the crude (meth)acrylic acid solution. Or, the producing process of the present invention may further comprise the step of dehydrating hydroxypropionic acid or 2-methyl-3-hydroxypropionic acid to convert to (meth)acrylic acid, thereby obtaining the crude (meth)acrylic acid solution. The crude (meth)acrylic acid solution used in the producing process of the present invention may be obtained by such processes.

The present invention also provides a process for producing a hydrophilic resin or an absorbent resin, comprising the step of polymerizing a monomeric component(s) including the (meth)acrylic acid obtained by the producing process of the present invention. When (meth)acrylic acid obtained by the producing process of the present invention is used as a monomer for producing a hydrophilic resin such as an absorbent resin and a water-soluble resin, the polymerization reaction is easily controlled and quality of the hydrophilic resin is stabilized, thereby improving various properties such as absorption performance and dispersibility of inorganic substances.

A crystallization system of the present invention comprises: a crystallizer provided with a heat-transfer surface and having a medium-present part and a crystal-present part partitioned by the heat-transfer surface; a heat source device provided with a cooling medium-supply port connected to an inlet of the medium-present part, and a cooling medium-return port connected to an outlet of the medium-present part; and a first buffer tank provided with an upper opening connected to the outlet of the medium-present part and the cooling medium-return port, and a lower opening connected to the cooling medium-supply port and/or the outlet of the medium-present part and the cooling medium-return port. By using this crystallization system, temperature of the cooling medium returned to the heat source device can be maintained constant. Therefore, cooling load of the heat source device is easily maintained constant when the crystallizing step is performed in the crystallizer, and as a result, the heat source device can stably work, crystallizing operation can be stabilized, and the consumption energy can be reduced.

An another crystallization system of the present invention comprises: a crystallizer provided with a heat-transfer surface and having a medium-present part and a crystal-present part partitioned by the heat-transfer surface; a heat source device provided with a heating medium-supply port connected to an inlet of the medium-present part, and a heating medium-return port connected to an outlet of the medium-present part; and a second buffer tank provided with an upper opening connected to the heating medium-supply port and/or the outlet of the medium-present part and the heating medium-return port, and a lower opening connected to the outlet of the medium-present part and the heating medium-return port. By using this crystallization system, temperature of the heating medium returned to the heat source device can be maintained constant. Therefore, heating load of the heat source device is easily maintained constant when the melting step is performed in the crystallizer, and as a result, the heat source device can stably work, melting operation can be stabilized, and the consumption energy can be reduced.

A still another crystallization system of the present invention comprises: a crystallizer provided with a heat-transfer surface and having a medium-present part and a crystal-present part partitioned by the heat-transfer surface; a first heat source device provided with a cooling medium-supply port connected to an inlet of the medium-present part, and a cooling medium-return port connected to an outlet of the medium-present part; a second heat source device provided with a heating medium-supply port connected to the inlet of the medium-present part, and a heating medium-return port connected to the outlet of the medium-present part; a first buffer tank provided with an upper opening connected to the outlet of the medium-present part and the cooling medium-return port, and a lower opening connected to the cooling medium-supply port and/or the outlet of the medium-present part and the cooling medium-return port; and a second buffer tank provided with an upper opening connected to the heating medium-supply port and/or the outlet of the medium-present part and the heating medium-return port, and a lower opening connected to the outlet of the medium-present part and the heating medium-return port. According to the above system, each temperature of the cooling medium and the heating medium returned to the heat source device can be maintained constant, the heat source device can stably work both in the crystallizing and melting operations, thereby stabilizing the crystallizing and melting operations, and the consumption energy can be reduced.

A still another crystallization system of the present invention comprises: a first crystallizer provided with a first heat-transfer surface and having a first medium-present part and a first crystal-present part partitioned by the first heat-transfer surface; a second crystallizer provided with a second heat-transfer surface and having a second medium-present part and a second crystal-present part partitioned by the second heat-transfer surface; a refrigerator provided with a cooling medium-supply port connected to an inlet of the first medium-present part, a cooling medium-return port connected to an outlet of the first medium-present part, a heating medium-supply port connected to an inlet of the second medium-present part, and a heating medium-return port connected to an outlet of the second medium-present part; a first buffer tank provided with an upper opening connected to the outlet of the first medium-present part and the cooling medium-return port, and a lower opening connected to the cooling medium-supply port and/or the outlet of the first medium-present part and the cooling medium-return port; and a second buffer tank provided with an upper opening connected to the heating medium-supply port and/or the outlet of the second medium-present part and the heating medium-return port, and a lower opening connected to the outlet of the second medium-present part and the heating medium-return port. When a refrigerator is employed as the heat source device, it becomes possible that the cooling medium discharged from the refrigerator are used in the crystallizing operation and the heating medium discharged from the refrigerator are used in the melting operation, and hence, the consumption energy for the crystallizing and melting operations can be decreased, and efficient performance of the crystallizing and melting operations can be realized.

In the first buffer tank and the second buffer tank, distance between the upper opening and the lower opening is preferably equal to or more than a maximum cross-section length thereof. Thereby, a temperature gradient is easily generated in the cooling medium or the heating medium retained in the buffer tank in a vertical direction, and it becomes easy to maintain the temperature of the cooling medium or the heating medium returned to the heat source device constant.

Advantageous Effects of Invention

According to the process for producing (meth)acrylic acid and the crystallization system of the present invention, temperature change of the cooling medium or the heating medium returned to the heat source device from the crystallizer is lessened, the heat source device can stably work, crystallizing operation and/or melting operation can be stabilized, and hence, the consumption energy can be reduced.

DESCRIPTION OF THE PREFERRED EMBODIMENTS

Figure 1:
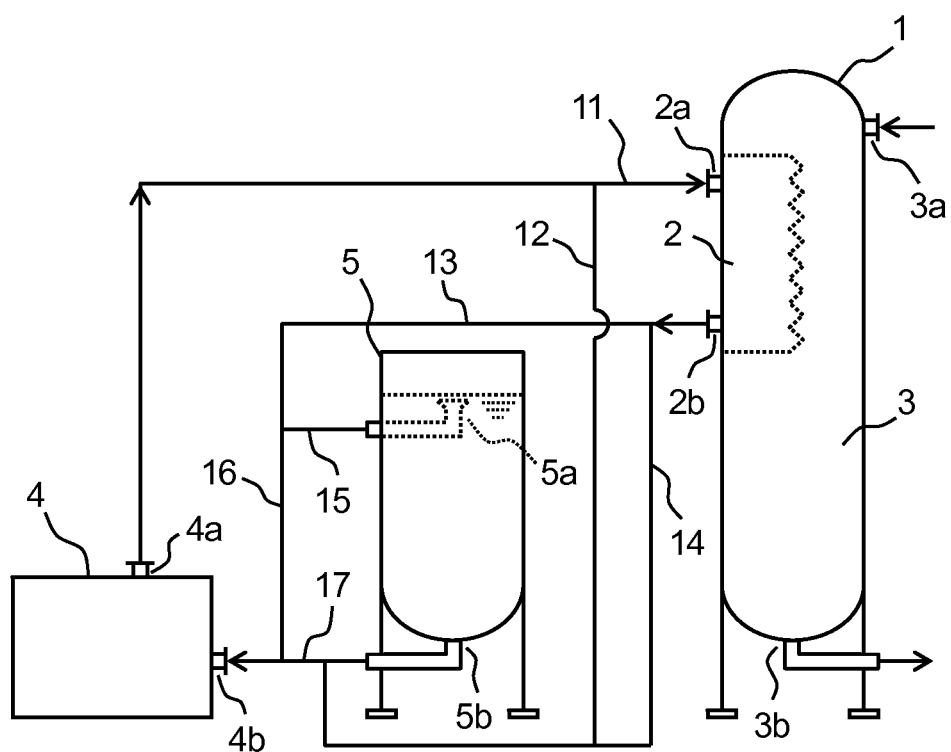
FIG. 1 shows a crystallization system comprising a heat source device which supplies a cooling medium, a crystallizer and a first buffer tank.

[1. A Process for Producing (Meth)Acrylic Acid]

A process for producing (meth)acrylic acid of the present invention comprises a step of supplying a cooling medium to a crystallizer from a heat source device, thereby crystallizing (meth)acrylic acid from a crude (meth)acrylic acid solution, that step may be hereinafter referred to as a "crystallizing step", and/or a step of supplying a heating medium to a crystallizer from a heat source device, thereby melting crystallized (meth)acrylic acid, that step may be hereinafter referred to as a "melting step".

In the crystallizing step, a crude (meth)acrylic acid solution is cooled by a cooling medium supplied to a crystallizer from a heat source device, thereby obtaining a (meth)acrylic acid crystal. The obtained (meth)acrylic acid crystal may be separated or collected by any solid-liquid separation means, or may be melted by any melting method. Preferably, the crystallized (meth)acrylic acid is melted by the below-described melting step.

No particular limitation is placed on the crude (meth)acrylic acid solution which is crystallized in the crystallizing step, and the crude (meth)acrylic acid solution can be any solution containing (meth)acrylic acid and an impurity thereof. Examples of the impurity include unreacted (meth)acrylic acid production raw materials, a collection liquid medium (e.g. water or the like), acetic acid, propionic acid, maleic acid, acetone, acrolein, furfural, formaldehyde and the like.

The crude (meth)acrylic acid solution preferably has (meth)acrylic acid concentration of 80 mass % or more, more preferably 90 mass % or more, and further more preferably 95 mass % or more. When the (meth)acrylic acid concentration is 80 mass % or more, crystallization of the crude (meth)acrylic acid solution is facilitated. Meanwhile, the upper limit of the (meth)acrylic acid concentration is not particularly limited.

In the melting step, crystallized (meth)acrylic acid is heated by a heating medium supplied to a crystallizer from a heat source device, thereby melting. The crystallized (meth)acrylic acid used in the melting step may be obtained in the above-described crystallizing step, or may be obtained by any crystallizing method. In the present invention, it is preferable that the (meth)acrylic acid crystal obtained in the crystallizing step is melted in the melting step.

In some cases, a sweating operation, by which the crystallized (meth)acrylic acid is partially melted and impurities present between the crystals or on the surface of the crystal are washed away, may be performed for the purpose of enhancing the purity of the (meth)acrylic acid melt when the crystallized (meth)acrylic acid is melted by heating; and in the present invention, the sweating operation is included in the melting step.

In the present invention, the crystallizing step and the melting step may be alternately repeated multiple times, thereby obtaining (meth)acrylic acid with higher purity.

Any heat source device can be used in the producing process of the present invention as long as the heat source device is capable of cooling the cooling medium and/or heating the heating medium. In the case where the heat source device supplies either the cooling medium or the heating medium, a heat source device for a cooling medium, that supplies the cooling medium, or a heat source device for a heating medium, that supplies the heating medium, is used as the heat source device. Examples of the heat source device include a multitubular heat exchanger in which liquefied gas or steam is used as a heat source.

The heat source device may be capable of both cooling the cooling medium and heating the heating medium. As such a heat source device, a refrigerator can be employed, and specifically, a refrigerator which supplies the cooling medium and the heating medium simultaneously is preferably used as the heat source device supplying the cooling medium and the heat source device supplying the heating medium. As the refrigerator, an absorption refrigerator (e.g. an ammonia absorption refrigerator, a water-lithium bromide refrigerator, and the like), a compression refrigerator, an adsorption refrigerator and the like can be used. When the refrigerator is used as the heat source device, both cold energy and heat energy from the refrigerator are utilized effectively, thereby reducing consumption energy of the heat source device.

The cooling medium and the heating medium are not particularly limited, as long as they are kept in liquid states in the heat source device and the crystallizer during producing (meth)acrylic acid. The cooling medium may be the same as or different from the heating medium. For example, in the case where the cooling medium and the heating medium are the same, ethylene glycol aqueous solution, glycerin aqueous solution, methanol aqueous solution, or the like is used as the cooling medium and the heating medium. For example, in the case where a part or all of the cooling medium is utilized as a source of the heating medium, and a part or all of the heating medium is utilized as a source of the cooling medium, as described below, the cooling medium and the heating medium are preferably the same.

In the case where the producing process of the present invention comprises the crystallizing step, the producing process of the present invention comprises the steps of: supplying a cooling medium to a crystallizer from a heat source device, thereby crystallizing (meth)acrylic acid from a crude (meth)acrylic acid solution; and discharging the cooling medium from the crystallizer and returning the cooling medium to the heat source device. The cooling medium which has been returned to the crystallizer is cooled by the heat source device and again supplied to the crystallizer.

Temperature of the cooling medium discharged from the heat source device is not particularly limited, as long as it is lower than the melting point of the crude (meth)acrylic acid solution. The melting point of the crude (meth)acrylic acid solution changes depending on the impurity composition and the (meth)acrylic acid concentration thereof. For example, a crude acrylic acid solution containing 80 mass % to 95 mass % of acrylic acid and water as a most component of impurity has a melting point of more than −5° C. and 13.5° C. or lower, generally.

The temperature of the cooling medium discharged from the heat source device is preferably −5° C. or lower, more preferably −10° C. or lower, and preferably −40° C. or higher, more preferably −30° C. or higher. As described above, the upper limit of the temperature of the cooling medium discharged from the heat source device is needed to be lower than the melting point of the crude (meth)acrylic acid solution; however, the temperature of the cooling medium discharged from the heat source device is preferably −5° C. or lower so that the amount of the cooling medium required for crystallizing is not too much increased and the size of the crystallizer, pipes for the cooling medium or the like is not too much increased. Meanwhile, if the temperature of the cooling medium discharged from the heat source device is lower than −40° C., it is likely that a heat source device with high-power specifications is needed or the energy consumption of the heat source device is increased due to increase in the cooling load of the heat source device; and hence, the temperature of the cooling medium discharged from the heat source device is preferably −40° C. or higher.

The above description concerns the case where the one cooling medium discharged from the heat source device is used; however, two or more cooling mediums, which have different temperatures from each other, may be used as the cooling medium discharged from the heat source device. For example, in the case where the cooling medium supplied from the heat source device includes a first cooling medium and a second cooling medium having lower temperature than the first cooling medium, the first cooling medium preferably has temperature of −15° C. or higher and −5° C. or lower, and the second cooling medium preferably has temperature of −40° C. or higher and lower than −15° C. In this case, the crystallizing step is preferably performed such that the first cooling medium is supplied to the crystallizer and then the second cooling medium having lower temperature than the first cooling medium is supplied to the crystallizer. When the first cooling medium and the second cooling medium are used in this manner, the purity of the (meth)acrylic acid crystal is easily enhanced and the energy consumption of the heat source device can be further reduced.

In the case where the producing process of the present invention comprises the melting step, the producing process of the present invention comprises the steps of: supplying a heating medium to a crystallizer from a heat source device, thereby melting crystallized (meth)acrylic acid; and discharging the heating medium from the crystallizer and returning the heating medium to the heat source device. The heating medium which has been returned to the crystallizer is heated by the heat source device and again supplied to the crystallizer.

Temperature of the heating medium discharged from the heat source device is not particularly limited, as long as it exceeds the melting point of the crystallized (meth)acrylic acid. The temperature of the heating medium discharged from the heat source device is preferably 20° C. or higher, more preferably 30° C. or higher, and preferably 45° C. or lower, more preferably 40° C. or lower. As described above, the lower limit of the temperature of the heating medium discharged from the heat source device is needed to be higher than the melting point of the crystallized (meth)acrylic acid; however, the temperature of the heating medium discharged from the heat source device is preferably 20° C. or higher so that the amount of the heating medium required for melting is not too much increased and the size of the crystallizer, pipes for the heating medium or the like is not too much increased. Meanwhile, in the case where the temperature of the heating medium discharged from the heat source device is higher than 45° C., continuous operation of the crystallizer may become difficult or the purity or yield of the obtained (meth)acrylic acid may decline, due to occurrence of polymerization of (meth)acrylic acid in the crystallizer. In addition, it is likely that a heat source device with high-power specifications is needed or the energy consumption of the heat source device is increased due to increase in the heating load of the heat source device. Therefore, the temperature of the heating medium discharged from the heat source device is preferably 45° C. or lower. In addition, two or more heating mediums, which have different temperatures from each other, may be used as the heating medium discharged from the heat source device.

The temperature of the cooling medium or the heating medium discharged from the heat source device is preferably maintained constant within a certain range, and the range of the temperature is preferably within 3.0° C., more preferably within 1.0° C. In addition, a flow rate of the cooling medium or the heating medium discharged from the heat source device is preferably maintained constant within a certain range. When the temperature and the flow rate of the cooling medium or the heating medium discharged from the heat source device are maintained constant, crystallizing and melting operations of the crystallizer is easily conducted stably. Further, in cooperation with the temperature of the cooling medium or the heating medium returned to the heat source device being maintained constant as described below, the cooling or heating load of the heat source device is easily maintained constant; and as a result, the heat source device can stably work and the consumption energy thereof can be reduced. The flow rate of the cooling medium or the heating medium discharged from the heat source device is set appropriately depending on the temperature of the cooling medium or the heating medium discharged from the heat source device, the amount and the temperature of the crude (meth)acrylic acid solution or the crystallized (meth)acrylic acid.

In the case where the producing process of the present invention comprises the crystallizing step and the melting step, the heat source device used in the crystallizing step may be the same as or different from the heat source device used in the melting step.

Any crystallizer can be used in the producing process of the present invention as long as the crystallizer is capable of crystallizing (meth)acrylic acid. In the case where the producing process of the present invention comprises the crystallizing step, the cooling medium is supplied to the crystallizer from the heat source device, thereby crystallizing (meth) acrylic acid from the crude (meth)acrylic acid solution. In the case where the producing process of the present invention comprises the melting step, the heating medium is supplied to the crystallizer from the heat source device, thereby melting crystallized (meth)acrylic acid.

The crystallizer used in the producing process of the present invention is preferably provided with a heat-transfer surface. In this case, the crystallizer preferably has a part where the cooling medium or the heating medium is supplied to (i.e. a medium-present part) and a part where the crude (meth)acrylic acid solution and/or the (meth)acrylic acid crystal is present (i.e. a crystal-present part), that are partitioned by the heat-transfer surface. In the case where the crystallizer is provided with the heat-transfer surface, the crude (meth)acrylic acid solution is supplied to the crystallizer while the cooling medium is supplied to the crystallizer in the crystallizing step, whereby the crude (meth)acrylic acid solution is cooled by the cooling medium via the heat-transfer surface, and (meth)acrylic acid is crystallized. In the melting step, the heating medium is supplied to the crystallizer, whereby the crystallized (meth)acrylic acid is heated by the heating medium via the heat-transfer surface to melt.

As the crystallizer having the heat-transfer surface, an apparatus used as a heat exchanger generally can be employed, and particularly, an apparatus used as a heat exchanger in which heat is exchanged between liquids is preferably employed. For example, a plate-type heat exchanger comprising a single plate or a plurality of plates stacked at intervals, wherein the medium-present part(s) and the crystal-present part(s) are alternately disposed while being separated by the plate(s); a multitubular (shell-and-tube) heat exchanger comprising a plurality of tubes in a vessel, wherein heat is exchanged between the interiors and exteriors of the tubes; a double-pipe heat exchanger comprising an outer pipe and an inner pipe disposed in the outer pipe, wherein heat is exchanged between the interior and exterior of the inner pipe; a coil heat exchanger comprising one coil-shaped tube disposed in a vessel, wherein heat is exchanged between the interior and exterior of the tube; a spiral plate exchanger comprising a center tube whose cross-section is divided into two parts and two heat exchanger plates winding the center tube in whorl, whereby two whorl-like paths are formed; or the like may be employed. A cross-sectional shape of the tubes used in the multitubular heat exchanger, the double-pipe heat exchanger, the coil heat exchanger and the spiral plate exchanger is not particularly limited.

In the crystallizing step, the cooling medium which has been supplied to the crystallizer receives heat by heat exchange with the crude (meth)acrylic acid solution, whereby the cooling medium is heated. Provided that temperature and a flow rate of the cooling medium supplied to the crystallizer is constant in the crystallizing step, the temperature of the cooling medium discharged from the crystallizer is high at the beginning of the crystallizing step and drops as the progress of crystallizing. The temperature of the cooling medium discharged from the crystallizer possibly varies in the range of, for example, about 50° C., though it depends on conditions. Therefore, when the cooling medium discharged from the crystallizer is directly returned to the heat source device, the temperature of the cooling medium returned to the heat source device changes greatly and the cooling load of the heat source device changes. As a result, the operation of the heat source device is destabilized, thereby destabilizing the crystallizing operation and increasing the consumption energy of the heat source device.

In the melting step, the heating medium which has been supplied to the crystallizer releases heat by heat exchange with crystallized (meth)acrylic acid, whereby the heating medium is cooled. Provided that temperature and a flow rate of the heating medium supplied to the crystallizer is constant in the melting step, the temperature of the heating medium discharged from the crystallizer is low at the beginning of the melting step and rises as the progress of melting. The temperature of the heating medium discharged from the crystallizer possibly varies in the range of, for example, about 50° C., though it depends on conditions. Therefore, when the heating medium discharged from the crystallizer is directly returned to the heat source device, the temperature of the heating medium returned to the heat source device changes greatly and the heating load of the heat source device changes. As a result, the operation of the heat source device is destabilized, thereby destabilizing the melting operation and increasing the consumption energy of the heat source device.

The reason that enlarging the temperature change of the cooling medium or the heating medium returned to the heat source device causes destabilization of the operation of the heat source device and increase in the consumption energy of the heat source device is explained as follows. A heat source device generally has a suitable load range where cooling or heating is efficiently performed, according to its specification. However, when the temperature of the cooling medium or the heating medium returned to the heat source device varies greatly, it happens that the heat source device is forced to work in an inefficient load range, resulting in increase in the consumption energy. In addition, when the heat source device works in an inefficient load range, the operation of the heat source device tends to destabilize. Further, the heat source device is generally chosen based on a maximum value of the cooling load of the cooling medium or the heating load of the heating medium; and hence, when the temperature of the cooling medium or the heating medium returned to the heat source device varies greatly, a heat source device with higher-power specifications, that has a higher cooling or heating capacity, is needed than when the temperature is constant. In this case, a larger equipment of the heat source device is required and it becomes more difficult for the heat source device to operate at a low load.

Therefore, in the process for producing (meth)acrylic acid of the present invention, first to fourth adjustment operations, which are described below, are employed for the purpose of reducing the range of the temperature change of the cooling medium or the heating medium returned to the heat source device, irrespective of the temperature change of the cooling medium or the heating medium discharged from the crystallizer. Specifically, in the crystallizing step, the temperature of the cooling medium returned to the heat source device is maintained constant by a first adjustment operation or a second adjustment operation, using a first buffer tank, and in the melting step, the temperature of the heating medium returned to the heat source device is maintained constant by a third adjustment operation or a fourth adjustment operation, using a second buffer tank.

In the present invention, a buffer tank in which the cooling medium is stored is referred to as a first buffer tank, and a buffer tank in which the heating medium is stored is referred to as a second buffer tank. The first buffer tank and the second buffer tank are referred to collectively as a buffer tank.

No limitation is placed on the buffer tank as long as the cooling medium or the heating medium can be stored in the buffer tank. It is preferred that the buffer tank retains a certain amount of the cooling medium or the heating medium, and the cooling medium or the heating medium retained in the buffer tank has a temperature gradient such that an upper part is high-temperature and a lower part is low-temperature. The amount of the cooling medium or the heating medium retained in the buffer tank is appropriately determined by the temperature and the amount of the cooling medium or the heating medium discharged from the heat source device, the performance of the heat source device, the temperature and the amount of the crude (meth)acrylic acid solution supplied to the crystallizer, the temperature of the cooling medium or the heating medium retained in the buffer tank, and the like.

The buffer tank is provided with openings at an upper part and a lower part thereof, through which the cooling medium passes. Distance between the opening at the upper part and the opening at the lower part of the buffer tank is preferably equal to or more than a maximum cross-section length of the buffer tank, more preferably more than twice the maximum cross-section length, and further more preferably more than four times the maximum cross-section length; and as a result, a temperature gradient is easily generated in the cooling medium or the heating medium retained in the buffer tank in a vertical direction, and it becomes easy to maintain the temperature of the cooling medium or the heating medium returned to the heat source device constant. Details of the shape of the buffer tank is explained below.

The present invention is hereinafter explained referring to drawings to facilitate understanding of the present invention, however, the present invention is not limited to the embodiment shown in the drawing.

Figure 2:
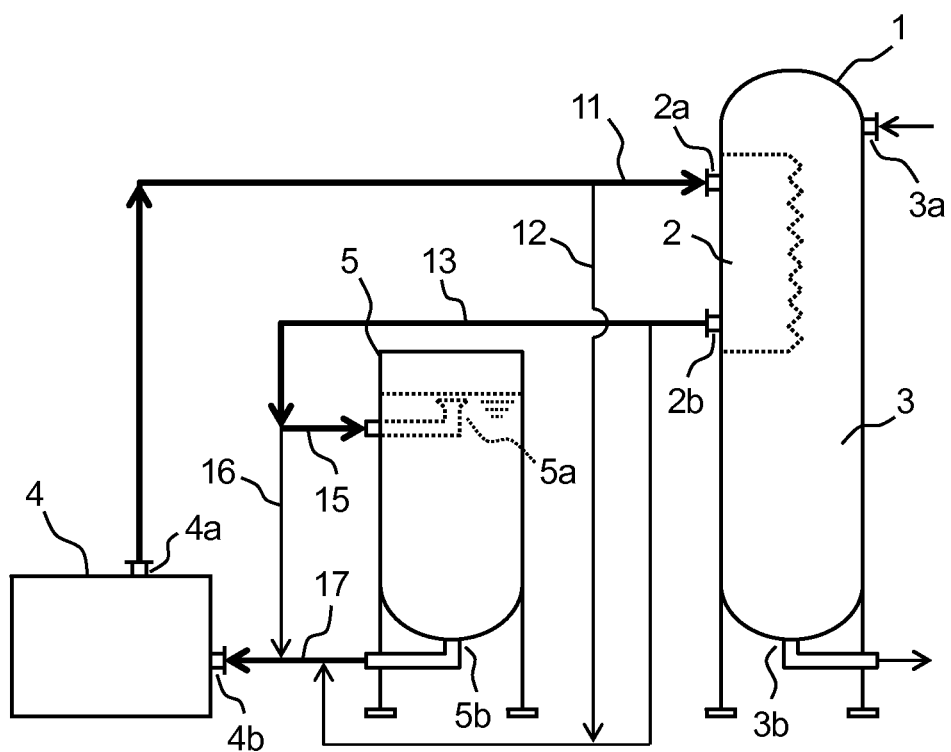
FIG. 2 shows a method for using the first buffer tank in the case where the cooling medium to be returned to the heat source device has high temperature.
Figure 3:
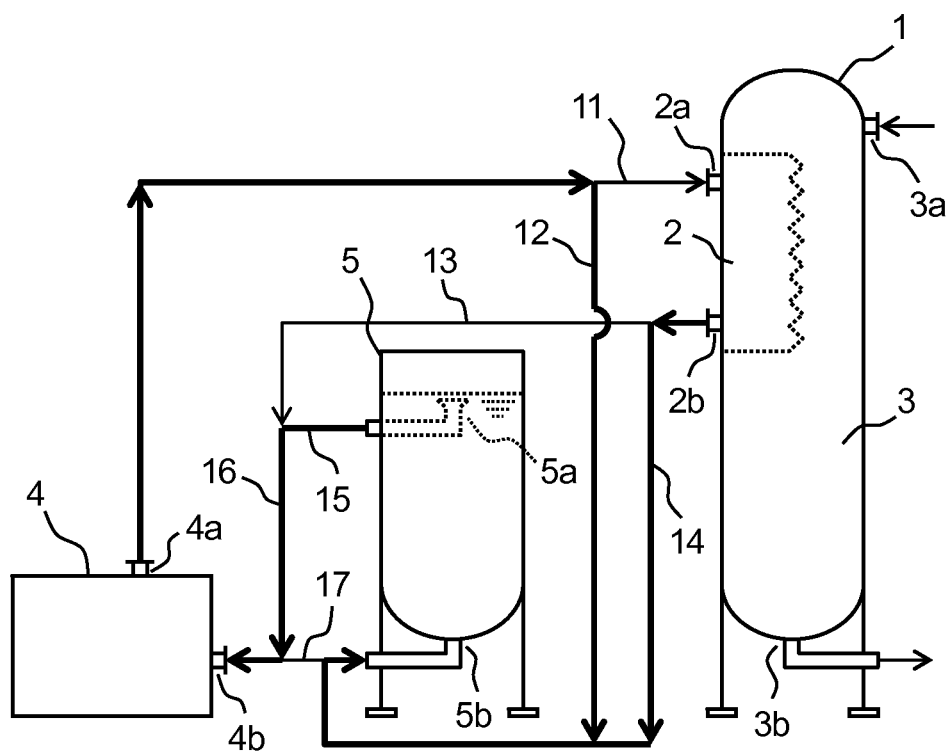
FIG. 3 shows a method for using the first buffer tank in the case where the cooling medium to be returned to the heat source device has low temperature.

A method for using the first buffer tank in the crystallizing step, the first adjustment operation, and the second adjustment operation are explained referring to FIGS. 1 to 3.

FIG. 1 shows flow paths connecting a heat source device a crystallizer, and a first buffer tank. A cooling medium discharged from a heat source device 4 is supplied to a crystallizer 1, heat-exchanged in the crystallizer 1, discharged from the crystallizer 1, and then returned to the heat source device 4. An upper opening 5a of a first buffer tank 5 is connected to a medium outlet 2b of the crystallizer 1 and a cooling medium-return port 4b of the heat source device 4. Further, a lower opening 5b of the first buffer tank 5 is connected to a cooling medium-supply port 4a and/or the medium outlet 2b of the crystallizer 1 and the cooling medium-return port 4b of the heat source device 4.

The first adjustment operation is explained referring to FIG. 2. The first adjustment operation is conducted when the temperature of the cooling medium to be returned to the heat source device is high in the crystallizing step.

For example, the temperature of the cooling medium discharged from the crystallizer 1 tends to be high at the beginning of the crystallizing step, and therefore, when this cooling medium discharged from the crystallizer 1 is directly returned to the heat source device 4, the high-temperature cooling medium comes to be returned to the heat source device 4. In this case, a flow through a path 16 is decreased by a valve or the like, and at least a part of the cooling medium to be returned to the heat source device 4 from the crystallizer 1 is fed into an upper part of a first buffer tank 5 through a path 15. Since the first buffer tank 5 retains a certain amount of the cooling medium having a temperature gradient such that the upper part is high-temperature and the lower part is low-temperature, when the high-temperature cooling medium is fed to the first buffer tank 5 through the upper opening 5a, the high-temperature cooling medium comes to be stored at the upper part of the first buffer tank 5 so as to keep the temperature gradient of the cooling medium in the first buffer tank 5. On the other hand, the low-temperature cooling medium is discharged from the lower opening 5b of the first buffer tank 5. On this occasion, it is preferred that the amount of the cooling medium in the first buffer tank 5 is maintained constant, and therefore, the amount of the cooling medium discharged from the lower part of the first buffer tank 5 is preferably equal to the amount of the cooling medium fed to the upper part of the first buffer tank 5. The low-temperature cooling medium discharged from the lower part of the first buffer tank 5 is returned to the heat source device 4 solely or along with the cooling medium discharged from the crystallizer 1 and carried through the path 16. Further, the low-temperature cooling medium discharged from the lower part of the first buffer tank 5 may be incorporated with a part of the cooling medium discharged from the heat source device 4 and carried thorough a path 12. Therefore, the cooling medium whose temperature has been adjusted to be lower than that of the cooling medium discharged from the crystallizer 1 is returned to the heat source device 4.

The second adjustment operation is explained referring to FIG. 3. The second adjustment operation is conducted when the temperature of the cooling medium to be returned to the heat source device is low in the crystallizing step.

For example, at the end of the crystallizing step, the temperature of the cooling medium discharged from the crystallizer 1 tends to be low, and therefore, when this cooling medium discharged from the crystallizer 1 is directly returned to the heat source device 4, the low-temperature cooling medium comes to be returned to the heat source device 4. In this case, a flow through a path 11 is decreased by a valve or the like, and at least a part of its flow is made to run through a path 12, whereby at least a part of the cooling medium to be supplied to the crystallizer 1 from the heat source device 4 is fed into the lower part of the first buffer tank 5. Or a flow through a path 13 is decreased and at least a part of its flow is made to run through a path 14, whereby at least a part of the cooling medium to be returned to the heat source device 4 from the crystallizer 1 is fed into the lower part of the first buffer tank 5. Since the first buffer tank 5 retains a certain amount of the cooling medium having the temperature gradient such that the upper part is high-temperature and the lower part is low-temperature, when the low-temperature cooling medium is fed to the first buffer tank 5 through the lower opening 5b, the low-temperature cooling medium comes to be stored at the lower part of the first buffer tank 5 so as to keep the temperature gradient of the cooling medium in the first buffer tank 5. On the other hand, the high-temperature cooling medium is discharged from the upper opening 5a of the first buffer tank 5. On this occasion, it is preferred that the amount of the cooling medium in the first buffer tank 5 is maintained constant, and therefore, the amount of the cooling medium discharged from the upper part of the first buffer tank 5 is preferably equal to the amount of the cooling medium fed to the lower part of the first buffer tank 5. The high-temperature cooling medium discharged from the upper part of the first buffer tank 5 is returned to the heat source device 4 solely or along with the cooling medium discharged from the crystallizer 1 and carried through the path 13. Therefore, the cooling medium whose temperature has been adjusted to be higher than that of the cooling medium discharged from the crystallizer 1 is returned to the heat source device 4. The high-temperature cooling medium discharged from the upper part of the first buffer tank 5 may be incorporated with a part of the cooling medium discharged from the heat source device 4 and carried thorough paths 12, 17.

According to the second adjustment operation, the cooling medium fed to the lower part of the first buffer tank 5 is at least a part of the cooling medium to be supplied to the crystallizer 1 from the heat source device 4 and/or at least a part of the cooling medium to be returned to the heat source device 4 from the crystallizer 1; and preferably, at least a part of the cooling medium to be supplied to the crystallizer 1 from the heat source device 4 is fed to the lower part of the first buffer tank 5. In this case, since the cooling medium to be supplied to the crystallizer 1 from the heat source device 4 has lower temperature than the cooling medium to be returned to the heat source device 4 from the crystallizer 1, the amount of cold energy per unit volume of the cooling medium stored at the lower part of the first buffer tank 5 is more increased, and therefore, it becomes possible to store the low-temperature cooling medium efficiently. In addition, the temperature of the cooling medium to be returned to the heat source device 4 from the crystallizer 1 varies depending on the progress of crystallizing; however, on the other hand, the temperature of the cooling medium to be supplied to the crystallizer 1 from the heat source device 4 is almost constant, and hence, it becomes easy to control the temperature of cooling medium stored at the lower part of the first buffer tank 5.

In the crystallizing step, the first buffer tank 5 may be in a state of not being used when the cooling medium to be returned to the heat source device 4 has temperature where the heat source device 4 is able to work efficiently. That is, in the crystallizing step, there may be a state that the cooling medium discharged from the crystallizer 1 is directly returned to the heat source device 4 without adopting the first or second adjustment operation.

According to the process for producing (meth)acrylic acid of the present invention, temperature of the cooling medium returned to the heat source device can be maintained constant within a certain range by the first and second adjustment operations. In the producing process of the present invention, the temperature change of the cooling medium returned to the heat source device is preferably within the range of 3.0° C., more preferably within the range of 1.0° C., and further more preferably within the range of 0.5° C. When the temperature change of the cooling medium returned to the heat source device is within the range of 3.0° C., the cooling load of the heat source device is easily maintained constant, resulting in stably working of the heat source device and reduction of the consumption energy of the heat source device.

Figure 4:
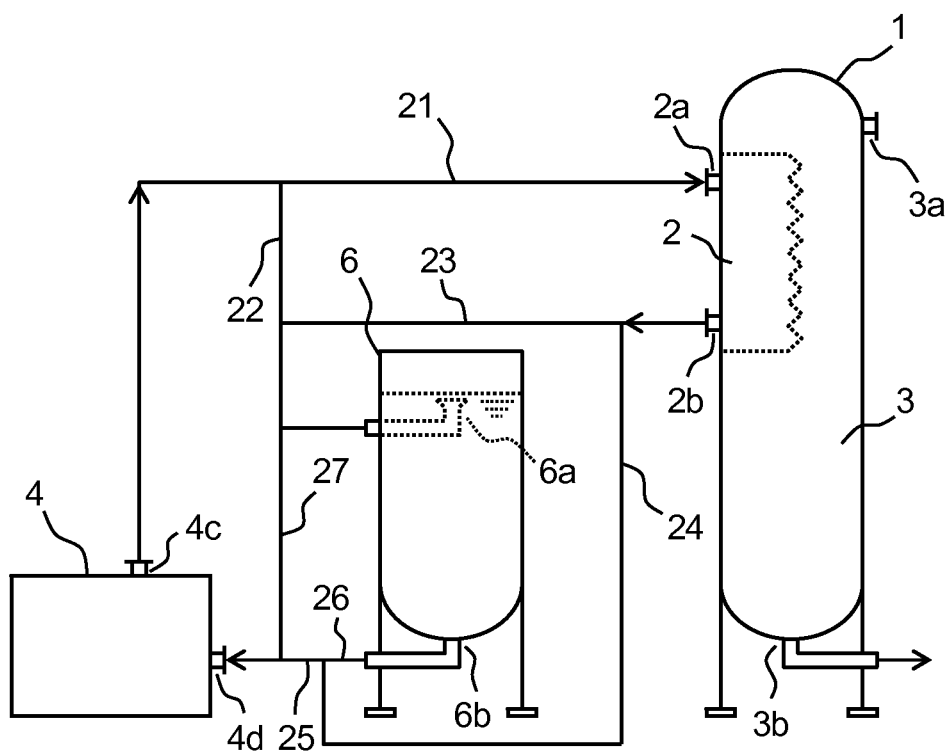
FIG. 4 shows a crystallization system comprising a heat source device which supplies a heating medium, a crystallizer and a second buffer tank.
Figure 5:
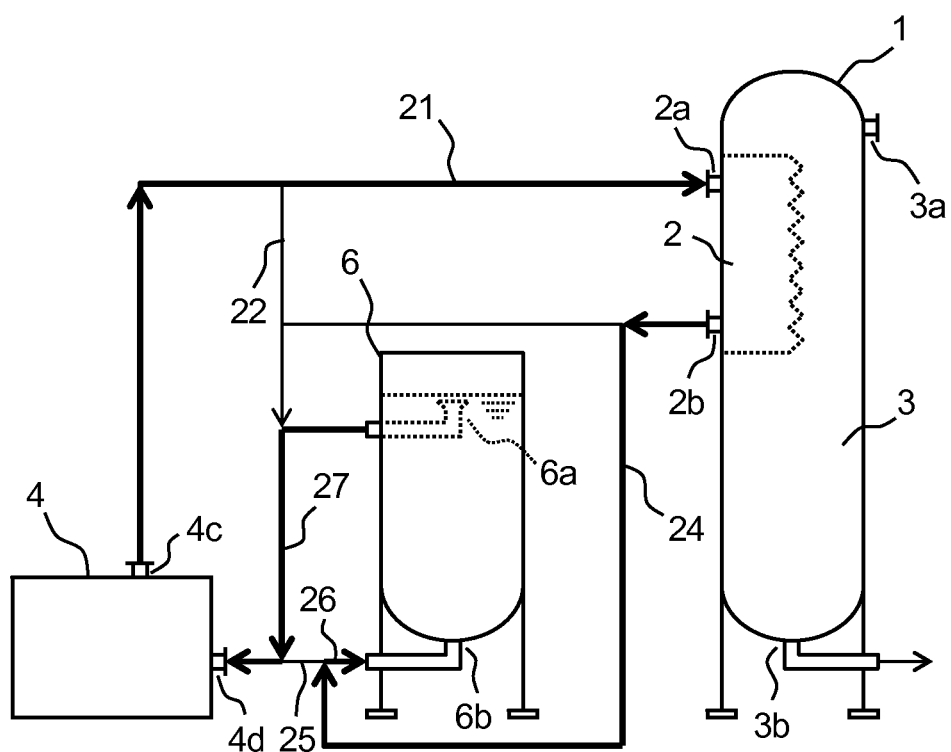
FIG. 5 shows a method for using the second buffer tank in the case where the heating medium to be returned to the heat source device has low temperature.
Figure 6:
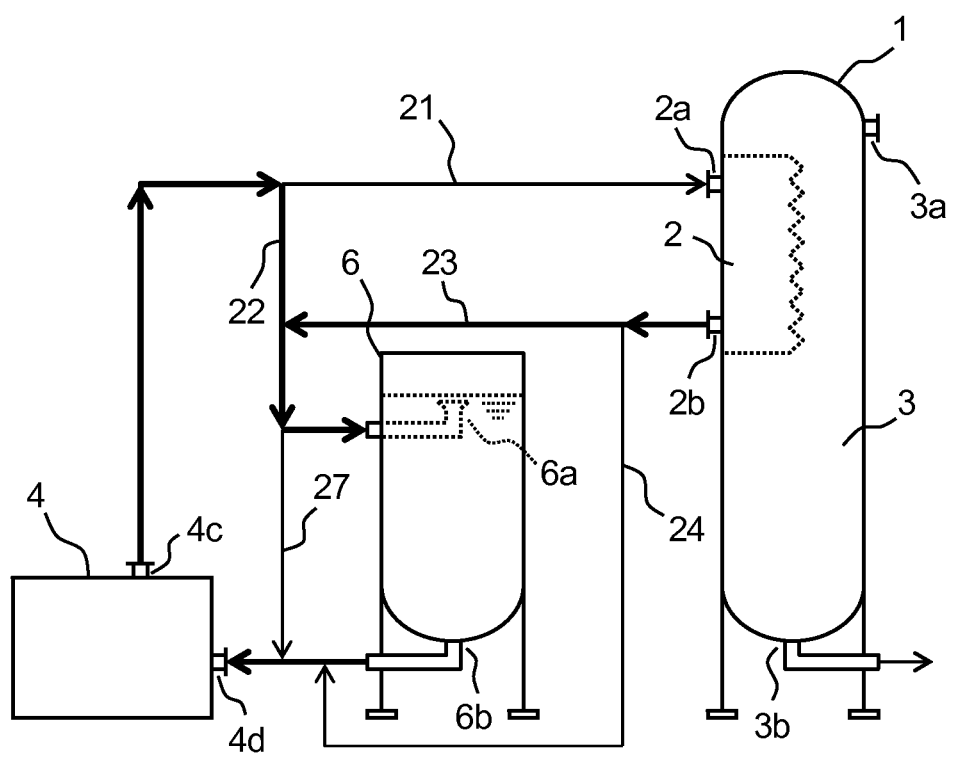
FIG. 6 shows a method for using the second buffer tank in the case where the heating medium to be returned to the heat source device has high temperature.

Next, a method for using the second buffer tank in the melting step, the third adjustment operation, and the fourth adjustment operation are explained referring to FIGS. 4 to 6.

FIG. 4 shows flow paths connecting a heat source device, a crystallizer and a second buffer tank. A heating medium discharged from a heat source device 4 is supplied to a crystallizer 1, heat-exchanged in the crystallizer 1, discharged from the crystallizer 1, and then returned to the heat source device 4. An upper opening 6a of a second buffer tank 6 is connected to a heating medium-supply port 4c and/or a medium outlet 2b of the crystallizer 1 and a heating medium-return port 4d of the heat source device 4. Further, a lower opening 6b of the second buffer tank 6 is connected to the medium outlet 2b of the crystallizer 1 and the heating medium-return port 4d of the heat source device 4.

The third adjustment operation is explained referring to FIG. 5. The third adjustment operation is conducted when the temperature of the heating medium to be returned to the heat source device is low in the melting step.

For example, the temperature of the heating medium discharged from the crystallizer 1 tends to be low at the beginning of the melting step, and therefore, when this heating medium discharged from the crystallizer 1 is directly returned to the heat source device 4, the low-temperature heating medium comes to be returned to the heat source device 4. In this case, a flow through a path 25 is decreased by a valve or the like, and at least a part of the heating medium to be returned to the heat source device 4 from the crystallizer 1 is fed into a lower part of a second buffer tank 6 through a path 26. Since the second buffer tank 6 retains a certain amount of the heating medium having a temperature gradient such that the upper part is high-temperature and the lower part is low-temperature, when the low-temperature heating medium is fed to the second buffer tank 6 through the lower opening 6b, the low-temperature heating medium comes to be stored at the lower part of the second buffer tank 6 so as to keep the temperature gradient of the heating medium in the second buffer tank 6. On the other hand, the high-temperature heating medium is discharged from the upper opening 6a of the second buffer tank 6. On this occasion, it is preferred that the amount of the heating medium in the second buffer tank 6 is maintained constant, and therefore, the amount of the heating medium discharged from the upper part of the second buffer tank 6 is preferably equal to the amount of the heating medium fed to the lower part of the second buffer tank 6. The high-temperature heating medium discharged from the upper part of the second buffer tank 6 is returned to the heat source device 4 solely or along with the heating medium discharged from the crystallizer 1 and carried through the path 25. Further, the high-temperature heating medium discharged from the upper part of the second buffer tank 6 may be incorporated with a part of the heating medium discharged from the heat source device 4 and carried thorough a path 22. Therefore, the heating medium whose temperature has been adjusted to be higher than that of the heating medium discharged from the crystallizer 1 is returned to the heat source device 4.

The fourth adjustment operation is explained referring to FIG. 6. The fourth adjustment operation is conducted when the temperature of the heating medium to be returned to the heat source device is high in the melting step.

For example, at the end of the melting step, the temperature of the heating medium discharged from the crystallizer 1 tends to be high, and therefore, when this heating medium discharged from the crystallizer 1 is directly returned to the heat source device 4, the high-temperature heating medium comes to be returned to the heat source device 4. In this case, a flow through a path 21 is decreased by a valve or the like, and at least a part of its flow is made to run through a path 22, whereby at least a part of the heating medium to be supplied to the crystallizer 1 from the heat source device 4 is fed into the upper part of the second buffer tank 6. Or a flow through a path 24 is decreased and at least a part of its flow is made to run through a path 23, whereby at least a part of the heating medium to be returned to the heat source device 4 from the crystallizer 1 is fed into the upper part of the second buffer tank 6. Since the second buffer tank 6 retains a certain amount of the heating medium having the temperature gradient such that the upper part is high-temperature and the lower part is low-temperature, when the high-temperature heating medium is fed to the second buffer tank 6 through the upper opening 6a, the high-temperature heating medium comes to be stored at the upper part of the second buffer tank 6 so as to keep the temperature gradient of the heating medium in the second buffer tank 6. On the other hand, the low-temperature heating medium is discharged from the lower opening 6b of the second buffer tank 6. On this occasion, it is preferred that the amount of the heating medium in the second buffer tank 6 is maintained constant, and therefore, the amount of the heating medium discharged from the lower part of the second buffer tank 6 is preferably equal to the amount of the heating medium fed to the upper part of the second buffer tank 6. The low-temperature heating medium discharged from the lower part of the second buffer tank 6 is returned to the heat source device 4 solely or along with the heating medium discharged from the crystallizer 1 and carried through the path 24. Therefore, the heating medium whose temperature has been adjusted to be lower than that of the heating medium discharged from the crystallizer 1 is returned to the heat source device 4. The low-temperature heating medium discharged from the lower part of the second buffer tank 6 may be incorporated with a part of the heating medium discharged from the heat source device 4 and carried thorough paths 22, 27.

According to the fourth adjustment operation, the heating medium fed to the upper part of the second buffer tank 6 is at least a part of the heating medium to be supplied to the crystallizer 1 from the heat source device 4 and/or at least a part of the heating medium to be returned to the heat source device 4 from the crystallizer 1; and preferably, at least a part of the heating medium to be supplied to the crystallizer 1 from the heat source device 4 is fed to the upper part of the second buffer tank 6. In this case, since the heating medium to be supplied to the crystallizer 1 from the heat source device 4 has higher temperature than the heating medium to be returned to the heat source device 4 from the crystallizer 1, the amount of heating energy per unit volume of the heating medium stored at the upper part of the second buffer tank 6 is more increased, and therefore, it becomes possible to store the high-temperature heating medium efficiently. In addition, the temperature of the heating medium to be returned to the heat source device 4 from the crystallizer 1 varies depending on the progress of melting; however, on the other hand, the temperature of the heating medium to be supplied to the crystallizer 1 from the heat source device 4 is almost constant, and hence, it becomes easy to control the temperature of heating medium stored at the upper part of the second buffer tank 6.

In the melting step, the second buffer tank 6 may be in a state of not being used when the heating medium to be returned to the heat source device 4 has temperature where the heat source device 4 is able to work efficiently. That is, in the melting step, there may be a state that the heating medium discharged from the crystallizer 1 is directly returned to the heat source device 4 without adopting the third or fourth adjustment operation.

According to the process for producing (meth)acrylic acid of the present invention, temperature of the heating medium returned to the heat source device can be maintained constant within a certain range by the third and fourth adjustment operations. In the producing process of the present invention, the temperature change of the heating medium returned to the heat source device is preferably within the range of 3.0° C., more preferably within the range of 1.0° C., and further more preferably within the range of 0.5° C. When the temperature change of the heating medium returned to the heat source device is within the range of 3.0° C., the heating load of the heat source device is easily maintained constant, resulting in stably working of the heat source device and reduction of the consumption energy of the heat source device.

It is preferred that the buffer tank is provided with a plurality of temperature measurement means arranged in a vertical direction of the buffer tank, whereby the amount of the cooling medium or the heating medium having high or low temperature in the buffer tank can be estimated. Further, it is preferred the temperature of the cooling medium or the heating medium returned to the heat source device is adjusted depending on the temperatures of the upper part and the lower part of the cooling medium or the heating medium retained in the buffer tank. The temperature of the cooling medium or the heating medium returned to the heat source device is adjusted preferably in a range where the heat source device does not unstably work and the consumption energy of the heat source device does not extremely increase. As the temperature measurement means, a conventionally-known temperature measurement means such as a thermometer and the like may be employed.

If the low-temperature cooling or heating medium retained in the buffer tank is depleted, whereby the high-temperature cooling or heating medium is suddenly returned to the heat source device, or the high-temperature cooling or heating medium retained in the buffer tank is depleted, whereby the low-temperature cooling or heating medium is suddenly returned to the heat source device, operation of the heat source device becomes very unstable. Thus, it is preferred that while measuring a temperature gradient in the vertical direction of the cooling or heating medium in the buffer tank, the temperature of the low-temperature cooling or heating medium returned to the heat source device is adjusted to be higher to decrease a flow rate of discharging the low-temperature cooling or heating medium from the buffer tank before the low-temperature cooling or heating medium is depleted. Or it is preferred that the temperature of the high-temperature cooling or heating medium returned to the heat source device is adjusted to be lower to decrease a flow rate of discharging the high-temperature cooling or heating medium from the buffer tank before the high-temperature cooling or heating medium is depleted.

Specifically, when the temperature of the lower part of the cooling or heating medium retained in the buffer tank exceeds a predetermined value, the temperature of the cooling or heating medium returned to the crystallizer is preferably adjusted to be higher; and when the temperature of the upper part of the cooling or heating medium retained in the buffer tank falls below a predetermined value, the temperature of the cooling or heating medium returned to the crystallizer is preferably adjusted to be lower. As a result, it becomes possible that the effects of the first to fourth adjustment operations are exerted for a longer period.

The process for producing (meth)acrylic acid of the present invention may comprise both the crystallizing step and the melting step. In this case, the process for producing (meth) acrylic acid of the present invention comprises the steps of: supplying a cooling medium to a crystallizer from a heat source device, thereby crystallizing (meth)acrylic acid from a crude (meth)acrylic acid solution; discharging the cooling medium from the crystallizer and returning the cooling medium to the heat source device; supplying a heating medium to the crystallizer from a heat source device, thereby melting the crystallized (meth)acrylic acid; and discharging the heating medium from the crystallizer and returning the heating medium to the heat source device. On this process, temperature of the cooling medium returned to the heat source device is maintained constant by the first adjustment operation or the second adjustment operation, and temperature of the heating medium returned to the heat source device is maintained constant by the third adjustment operation or the fourth adjustment operation. The heat source device used in the crystallizing step may be the same as or different from the heat source device used in the melting step.

Figure 7:
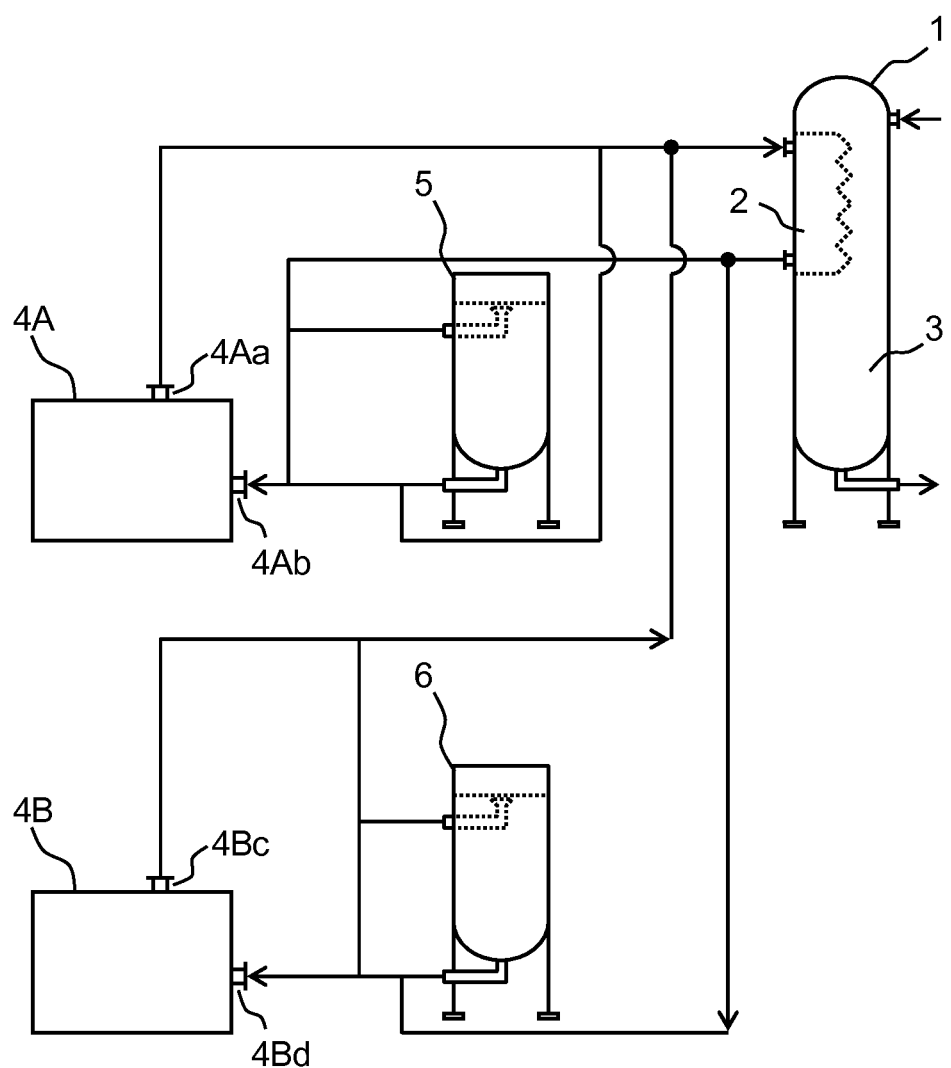
FIG. 7 shows a crystallization system comprising two heat source devices, one crystallizer and two buffer tanks.

FIG. 7 shows a process for producing (meth)acrylic acid comprising the crystallizing step and the melting step wherein the heat source device used in the crystallizing step is different from the heat source device used in the melting step. In FIG. 7, a first heat source device 4A which cools the cooling medium and a second heat source device 4B which heats the heating medium are depicted. The first heat source device 4A is provided with a cooling medium-supply port 4A$a$ and a cooling medium-return port 4A$b$, and the second heat source device 4B is provided with a heating medium-supply port 4B$c$ and a heating medium-return port 4B$d$.

The process for producing (meth)acrylic acid of the present invention shown in FIG. 7 comprises the steps of: supplying a cooling medium to a crystallizer 1 from the first heat source device 4A, thereby crystallizing (meth)acrylic acid from a crude (meth)acrylic acid solution; discharging the cooling medium from the crystallizer 1 and returning the cooling medium to the first heat source device 4A; supplying a heating medium to the crystallizer 1 from the second heat source device 4B, thereby melting the crystallized (meth)acrylic acid; and discharging the heating medium from the crystallizer 1 and returning the heating medium to the second heat source device 4B. In the embodiment shown in FIG. 7, the crystallizing step and the melting step are alternated in the crystallizer 1. Thus, the cooling medium and the heating medium are not supplied to the crystallizer 1 at the same time.

Temperature of the cooling medium returned to the heat source device 4A is maintained constant by the above-described first or second adjustment operation using the first buffer tank 5, and temperature of the heating medium returned to the heat source device 4B is maintained constant by the above-described third or fourth adjustment operation using the second buffer tank 6. In FIG. 7, a path through which at least a part of the cooling medium to be returned to the first heat source device 4A from the crystallizer 1 is fed to the lower part of the first buffer tank 5, that concerns the second adjustment operation, is omitted, and a path through which at least a part of the heating medium to be returned to the second heat source device 4B from the crystallizer 1 is fed to the upper part of the second buffer tank 6, that concerns the fourth adjustment operation, is omitted.

In the case where a refrigerator is used as the heat source device, the process for producing (meth)acrylic acid of the present invention may be performed such that the cooling medium is supplied to a first crystallizer from a refrigerator, thereby conducting the crystallizing step in the first crystallizer, as well as the heating medium is supplied to a second crystallizer from the refrigerator, thereby conducting the melting step in the second crystallizer. This embodiment is explained referring to FIG. 8.

A cooling medium is supplied from a refrigerator 7 through a cooling medium-supply port 7$a$ and returned to the refrigerator 7 through a cooling medium-return port 7$b$, and a heating medium is supplied from the refrigerator 7 through a heating medium-supply port 7$c$ and returned to the refrigerator 7 through a heating medium-return port 7$d$. The process for producing (meth)acrylic acid of the present invention shown in FIG. 8 comprises the steps of: supplying a cooling medium to a first crystallizer 1A from the refrigerator 7, thereby crystallizing (meth)acrylic acid from a crude (meth) acrylic acid solution; discharging the cooling medium from the first crystallizer 1A and returning the cooling medium to the refrigerator 7; supplying a heating medium to a second crystallizer 1B from the refrigerator 7, thereby melting crystallized (meth)acrylic acid; and discharging the heating medium from the second crystallizer 1B and returning the heating medium to the refrigerator 7.

Figure 8:
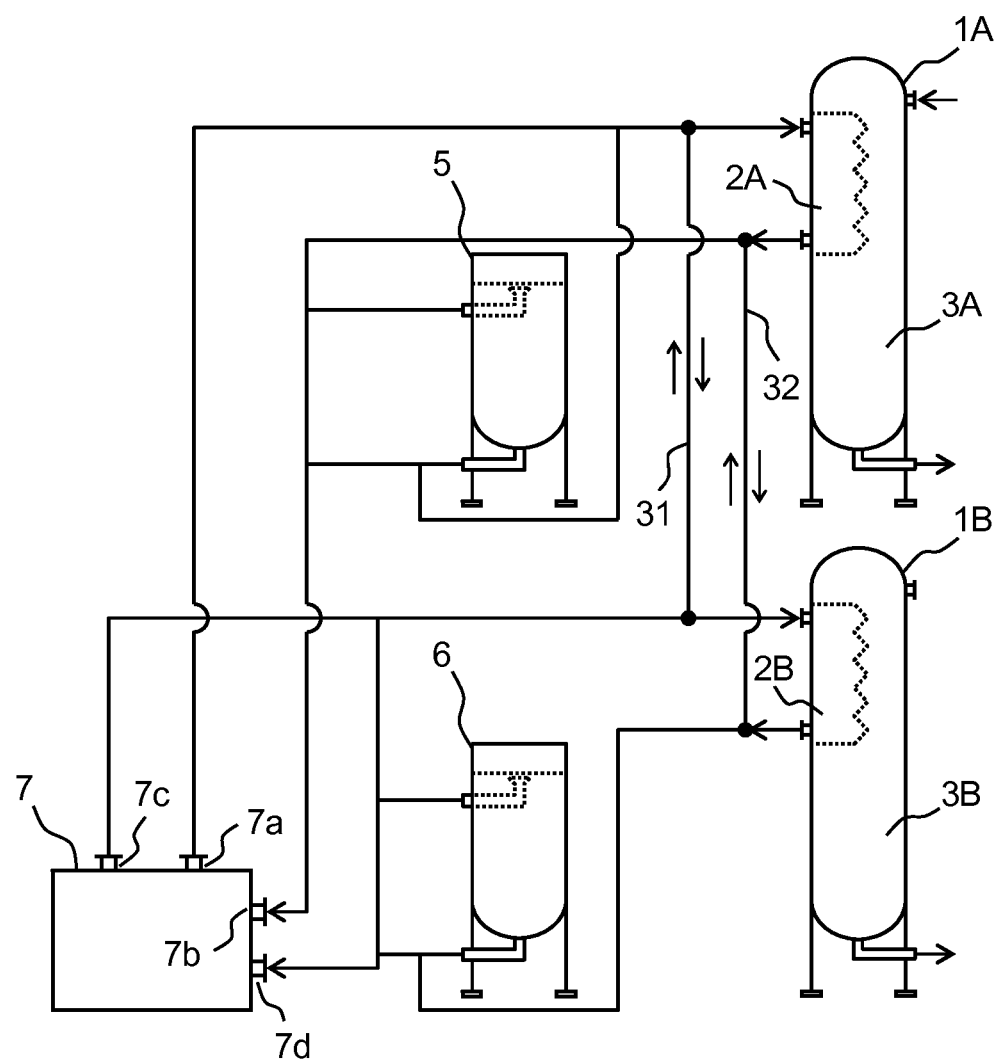
FIG. 8 shows a crystallization system comprising one refrigerator, two crystallizers and two buffer tanks.

Temperature of the cooling medium returned to the refrigerator 7 is maintained constant by the above-described first or second adjustment operation using a first buffer tank 5, and temperature of the heating medium returned to the refrigerator 7 is maintained constant by the above-described third or fourth adjustment operation using a second buffer tank 6. In FIG. 8, a path through which at least a part of the cooling medium to be returned to the refrigerator 7 from the crystallizer is fed to the lower part of the first buffer tank 5, that concerns the second adjustment operation, is omitted, and a path through which at least a part of the heating medium to be returned to the refrigerator 7 from the crystallizer is fed to the upper part of the second buffer tank 6, that concerns the fourth adjustment operation, is omitted.

After the crystallizing step in the first crystallizer 1A and the melting step in the second crystallizer 1B are finished, it is preferred that the cooling medium is supplied to the second crystallizer 1B and the heating medium is supplied to the first crystallizer 1A through a path 31, while the cooling medium discharged from the second crystallizer 1B is returned to the cooling medium-return port 7$b$ of the refrigerator 7 and the heating medium discharged from the first crystallizer 1A is returned to the heating medium-return port 7$d$ of the refrigerator 7 through a path 32. That is, it is preferred that: the heating medium is supplied to the first crystallizer 1A from the refrigerator 7, thereby conducting the melting step in the first crystallizer 1A, and discharged from the first crystallizer 1A to be returned to the refrigerator 7; and the cooling medium is supplied to the second crystallizer 1B from the refrigerator 7, thereby conducting the crystallizing step in the second crystallizer 1B, and discharged from the second crystallizer 1B to be returned to the refrigerator 7. In FIG. 8, each of the paths 31 and 32 has a path for the cooling medium and a path for the heating medium.

According to the embodiment shown in FIG. 8, it becomes possible that both the cooling medium and the heating medium supplied from the refrigerator 7 are utilized for the production of (meth)acrylic acid, and hence, the consumption energy for the production of (meth)acrylic acid can be decreased. Further, efficient production of (meth)acrylic acid is realized by combining the refrigerator 7, the first crystallizer 1A, the second crystallizer 1B, the first buffer tank 5 and the second buffer tank 6.

In the case where the cooling medium is supplied to the first crystallizer 1A from the refrigerator 7, thereby conducting the crystallizing step in the first crystallizer 1A, as well as the heating medium is supplied to the second crystallizer 1B from the refrigerator 7, thereby conducting the melting step in the second crystallizer 1B, as shown in FIG. 8, a part or all of the cooling medium discharged from the first crystallizer 1A may be utilized as a source of the heating medium to be supplied to the second crystallizer 1B, and a part or all of the heating medium discharged from the second crystallizer 1B may be utilized as a source of the cooling medium to be supplied to the first crystallizer 1A, in the process for producing (meth) acrylic acid of the present invention. In detail, when the temperature of the cooling medium discharged from the first crystallizer 1A is high, the cooling medium may be returned to the heating medium-return port 7$d$ of the refrigerator 7 through the path 32, and when the temperature of the heating medium discharged from the second crystallizer 1B is low, the heating medium may be returned to the cooling medium-return port 7$b$ of the refrigerator 7 through the path 32. On this occasion, the high-temperature cooling medium discharged from the first crystallizer 1A is preferably returned to the refrigerator 7 via the second buffer tank 6, and the low-temperature heating medium discharged from the second crystallizer 1B is preferably returned to the refrigerator 7 via the first buffer tank 5. This embodiment is explained below in more detail.

At the beginning of the crystallizing step, the temperature of the cooling medium discharged from the first crystallizer tends to be high. In addition, in the case where the melting step is conducted in the first crystallizer prior to the crystallizing step, high-temperature residual heat remains in the first crystallizer due to the influence of the high-temperature heating medium used in the melting step. As a result, at the beginning of the crystallizing step, the temperature of the cooling medium discharged from the first crystallizer tends to be high. In this case, if the temperature of the cooling medium is overly high, it is likely that the low-temperature cooling medium retained in the first buffer tank is rapidly consumed by the first adjustment operation and the temperature of the cooling medium returned to the heat source device (refrigerator) becomes difficult to be maintained constant within a certain range. As a result, the operation of the heat source device (refrigerator) is destabilized and the consumption energy of the heat source device increases.

At the beginning of the melting step, the temperature of the heating medium discharged from the second crystallizer tends to be low. In addition, in the case where the crystallizing step is conducted in the second crystallizer prior to the melting step, low-temperature residual heat remains in the second crystallizer due to the influence of the low-temperature cooling medium used in the crystallizing step. As a result, at the beginning of the melting step, the temperature of the heating medium discharged from the second crystallizer tends to be low. In this case, if the temperature of the heating medium is overly low, it is likely that the high-temperature heating medium retained in the second buffer tank is rapidly consumed by the third adjustment operation and the temperature of the heating medium returned to the heat source device (refrigerator) becomes difficult to be maintained constant within a certain range. As a result, the operation of the heat source device (refrigerator) is destabilized and the consumption energy of the heat source device increases.

Therefore, in the above cases, it is preferred that the high-temperature cooling medium discharged from the first crystallizer is utilized as a source of the heating medium to be supplied to the second crystallizer and the low-temperature heating medium discharged from the second crystallizer is utilized as a source of the cooling medium to be supplied to the first crystallizer. As a result, it becomes possible that the effects of the first and third adjustment operations are exerted for a longer period. In addition, the capacity of the buffer tank is able to be lessened, thereby reducing the construction cost. Further, the operation of the heat source device (refrigerator) can be stabilized and the consumption energy of the heat source device (refrigerator) can be decreased.

The high-temperature cooling medium discharged from the first crystallizer 1A is preferably returned to the heating medium-return port 7d of the refrigerator 7 through the path 32 to be utilized as the source of the heating medium. The high-temperature cooling medium discharged from the first crystallizer 1A is preferably returned to the heating medium-return port 7d via the second buffer tank 6. However, the cooling medium discharged from the first crystallizer 1A may be directly returned to the heating medium-return port 7d without flowing through the second buffer tank 6, depending on its temperature. The high-temperature cooling medium discharged from the first crystallizer 1A may be fed to the upper part or the lower part of the second buffer tank 6, depending on its temperature. Further, a part of the high-temperature cooling medium discharged from the first crystallizer 1A may be fed to the second buffer tank 6 and the rest part of that may be directly returned to the heating medium-return port 7d.

The low-temperature heating medium discharged from the second crystallizer 1B is preferably returned to the cooling medium-return port 7b of the refrigerator 7 through the path 32 to be utilized as the source of the cooling medium. The low-temperature heating medium discharged from the second crystallizer 1B is preferably returned to the cooling medium-return port 7b via the first buffer tank 5. However, the heating medium discharged from the second crystallizer 1B may be directly returned to the cooling medium-return port 7b without flowing through the first buffer tank 5, depending on its temperature. The low-temperature heating medium discharged from the second crystallizer 1B may be fed to the upper part or the lower part of the first buffer tank 5, depending on its temperature. Further, a part of the low-temperature heating medium discharged from the second crystallizer 1B may be fed to the first buffer tank 5 and the rest part of that may be directly returned to the cooling medium-return port 7b.

Concerning a rule for utilizing the cooling medium and the heating medium as the mutual sources, the following first rule for the mutual utilization is preferably employed that: the cooling medium discharged from the first crystallizer is utilized as the source of the heating medium when the temperature of the cooling medium discharged from the first crystallizer is higher than that of the heating medium discharged from the second crystallizer; and the heating medium discharged from the second crystallizer is utilized as the source of the cooling medium when the temperature of the heating medium discharged from the second crystallizer is lower than that of the cooling medium discharged from the first crystallizer.

Concerning the rule for utilizing the cooling medium and the heating medium as the mutual sources, the following second rule for the mutual utilization is also preferably employed that: the cooling medium discharged from the first crystallizer is utilized as the source of the heating medium when the temperature of the cooling medium discharged from the first crystallizer is higher than a predetermined temperature Ta between the temperature of the cooling medium supplied from the heat source device (refrigerator) and the temperature of the heating medium supplied from the heat source device (refrigerator); and the heating medium discharged from the second crystallizer is utilized as the source of the cooling medium when the temperature of the heating medium discharged from the second crystallizer is lower than the predetermined temperature Ta between the temperature of the cooling medium supplied from the heat source device (refrigerator) and the temperature of the heating medium supplied from the heat source device (refrigerator). Here, in the case where both temperatures of the cooling medium and the heating medium are equal to the temperature Ta, the cooling medium and the heating medium are allowed to be utilized as either source of the heating medium or the cooling medium. The temperature Ta is determined appropriately in accordance with balance of the amounts of utilizing the cooling medium and the heating medium as the mutual sources, and, for example, an average value of the temperatures of the cooling medium and the heating medium supplied from the heat source device (refrigerator) may be adopted as the temperature Ta. In the case of employing the second rule for the mutual utilization, it could be that both the cooling medium discharged from the first crystallizer and the heating medium discharged from the second crystallizer are utilized as the source of the cooling medium or the source of the heating medium.

In the process for producing (meth)acrylic acid in the present invention, the cooling medium may include a first cooling medium and a second cooling medium whose temperature is lower than the temperature of the first cooling medium. For example, a refrigerator supplying the first cooling medium, the second cooling medium and a heating medium is used, and (meth)acrylic acid may be produced by combining three crystallizers with this refrigerator. In this case, a crude (meth)acrylic acid solution is cooled by the first cooling medium, thereby conducting a former part of the crystallizing step, and a cooled crude (meth)acrylic acid solution is crystallized by the second cooling medium, thereby conducting a latter part of the crystallizing step. When the first cooling medium and the second cooling medium are provided like this, saving of energy in the crystallizing step can be achieved. In the former part of the crystallizing step, a part of (meth)acrylic acid may be crystallized when the crude (meth)acrylic acid is cooled by the first cooling medium. This embodiment is explained referring to FIG. 9.

A first cooling medium is supplied from a refrigerator 7 through a first cooling medium-supply port $7a_1$ and returned to the refrigerator 7 through a first cooling medium-return port $7b_1$, a second cooling medium is supplied from the refrigerator 7 through a second cooling medium-supply port $7a_2$ and returned to the refrigerator 7 through a second cooling medium-return port $7b_2$, and a heating medium is supplied from the refrigerator 7 through a heating medium-supply port $7c$ and returned to the refrigerator 7 through a heating medium-return port $7d$. The process for producing (meth)acrylic acid of the present invention shown in FIG. 9 comprises the steps of: supplying a first cooling medium to a first crystallizer 1A from the refrigerator 7, thereby cooling a crude (meth)acrylic acid solution; discharging the first cooling medium from the first crystallizer 1A and returning the first cooling medium to the refrigerator 7; supplying a second cooling medium to a second crystallizer 1B from the refrigerator 7, thereby crystallizing (meth)acrylic acid from a cooled crude (meth)acrylic acid solution; discharging the second cooling medium from the second crystallizer 1B and returning the second cooling medium to the refrigerator 7; supplying a heating medium to a third crystallizer 1C from the refrigerator 7, thereby melting crystallized (meth)acrylic acid; and discharging the heating medium from the third crystallizer 1C and returning the heating medium to the refrigerator 7. In this case, the former part of the crystallizing step is performed in the first crystallizer 1A, the latter part of the crystallizing step is performed in the second crystallizer 1B, and the melting step is performed in the third crystallizer 1C.

Figure 9:
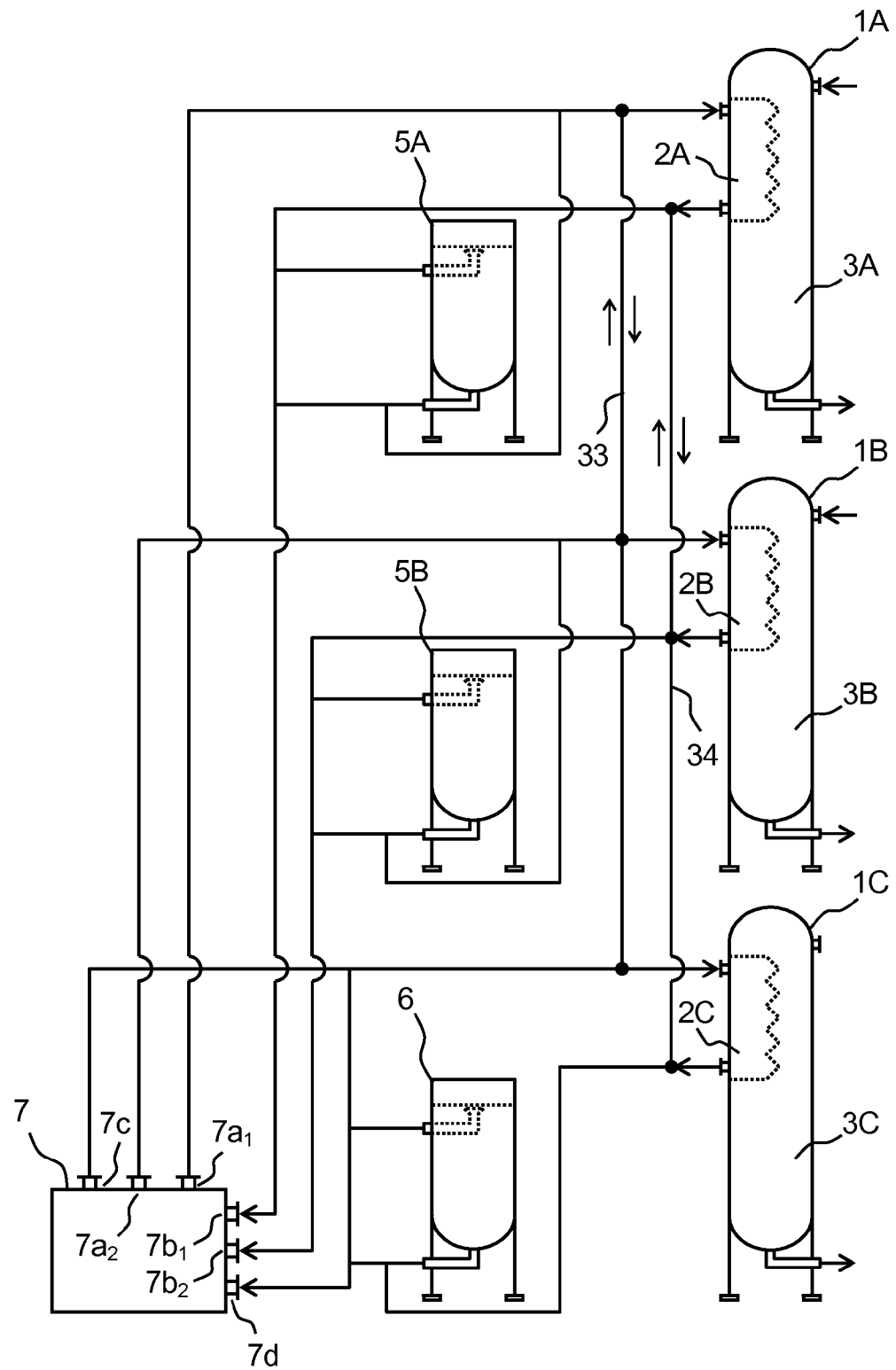
FIG. 9 shows a crystallization system comprising one refrigerator, three crystallizers and three buffer tanks.

Temperature of the first cooling medium returned to the refrigerator 7 is maintained constant by the above-described first or second adjustment operation using a first buffer tank (1) 5A, temperature of the second cooling medium returned to the refrigerator 7 is maintained constant by the above-described first or second adjustment operation using a first buffer tank (2) 5B, and temperature of the heating medium returned to the refrigerator 7 is maintained constant by the above-described third or fourth adjustment operation using a second buffer tank 6. In FIG. 9, paths through which at least a part of the cooling medium to be returned to the refrigerator 7 from the crystallizer is fed to the lower parts of the first buffer tanks 5A and 5B, that concerns the second adjustment operation, are omitted, and a path through which at least a part of the heating medium to be returned to the refrigerator 7 from the crystallizer is fed to the upper part of the second buffer tank 6, that concerns the fourth adjustment operation, is omitted.

After the former part of the crystallizing step in the first crystallizer 1A, the latter part of the crystallizing step in the second crystallizer 1B, and the melting step in the third crystallizer 1C are finished, the second cooling medium is supplied to the first crystallizer 1A, the heating medium is supplied to the second crystallizer 1B, and the first cooling medium is supplied to the third crystallizer 1C through a path 33, while the second cooling medium discharged from the first crystallizer 1A is returned to the second cooling medium-return port $7b_2$ of the refrigerator 7, the heating medium discharged from the second crystallizer 1B is returned to the heating medium-return port $7d$ of the refrigerator 7, and the first cooling medium discharged from the third crystallizer 1C is returned to the first cooling medium-return port $7b_1$ of the refrigerator 7 through a path 34. As a result, the latter part of the crystallizing step is performed in the first crystallizer 1A, the melting step is performed in the second crystallizer 1B, and the former part of the crystallizing step is performed in the third crystallizer 1C.

After the latter part of the crystallizing step in the first crystallizer 1A, the melting step in the second crystallizer 1B, and the former part of the crystallizing step in the third crystallizer 1C are finished, the heating medium is supplied to the first crystallizer 1A, the first cooling medium is supplied to the second crystallizer 1B, and the second cooling medium is supplied to the third crystallizer 1C through the path 33, while the heating medium discharged from the first crystallizer 1A is returned to the heating medium-return port $7d$ of the refrigerator 7, the first cooling medium discharged from the second crystallizer 1B is returned to the first cooling medium-return port $7b_1$ of the refrigerator 7, and the second cooling medium discharged from the third crystallizer 1C is returned to the second cooling medium-return port $7b_2$ of the refrigerator 7 through the path 34. As a result, the melting step is performed in the first crystallizer 1A, the former part of the crystallizing step is performed in the second crystallizer 1B, and the latter part of the crystallizing step is performed in the third crystallizer 1C.

In FIG. 9, each of the paths 33 and 34 has a path for the first cooling medium, a path for the second cooling medium and a path for the heating medium.

According to the embodiment shown in FIG. 9, (meth)acrylic acid can be more efficiently produced by combining the refrigerator 7, the first crystallizer 1A, the second crystallizer 1B, the third crystallizer 1C, the first buffer tank 5 and the second buffer tank 6; and the consumption energy of the crystallizer 7 can be further decreased.

Also in the embodiment shown in FIG. 9, the cooling medium and the heating medium may be utilized as the mutual sources. In this case, a part or all of the first cooling medium discharged from the first crystallizer 1A may be utilized as a source of the heating medium to be supplied to the third crystallizer 1C, and a part or all of the heating medium discharged from the third crystallizer 1C may be utilized as a source of the first cooling medium to be supplied to the first crystallizer 1A and/or the second cooling medium to be supplied to the second crystallizer 1B. In detail, when the temperature of the first cooling medium discharged from the first crystallizer 1A is high, the first cooling medium may be returned to the heating medium-return port $7d$ of the refrigerator 7 through the path 34, and when the temperature of the heating medium discharged from the third crystallizer 1C is low, the heating medium may be returned to the first cooling medium-return port $7b_1$ and/or the second cooling medium-return port $7b_2$ of the refrigerator 7 through the path 34.

For example, soon after the start of the former part of the crystallizing step in the first crystallizer, the first cooling medium tends to receive a larger amount of heat from the crude (meth)acrylic acid solution, and hence, the temperature T12 of the first cooling medium discharged from the first crystallizer tends to be high. Also, soon after the start of the melting step in the third crystallizer, the heating medium tends to release a larger amount of heat to the crystallized (meth)acrylic acid, and hence, the temperature T32 of the heating medium discharged from the third crystallizer tends to be low. Further, at the moment soon after the start of the melting step, low-temperature residual heat may remain in the third crystallizer due to the influence of the extremely low-temperature cooling medium (the second cooling medium) used in the preceding step thereof, and as a result, the temperature T32 of the heating medium discharged from the third crystallizer is likely to be low. Therefore, at the moment soon after the start of the respective steps, it could be that the temperature T32 of the heating medium discharged from the third crystallizer becomes lower than the temperature T12 of the first cooling medium discharged from the first crystallizer and the temperature T22 of the second cooling medium discharged from the second crystallizer. Here, the temperature T12 of the first cooling medium discharged from the first crystallizer is generally higher than the temperature T22 of the second cooling medium discharged from the second crystallizer. Thus, at the moment soon after the start of the respective steps, the inequality: T12>T22>T32 could be satisfied. In such a case, it is preferred that the first cooling medium discharged from the first crystallizer is utilized as a source of the heating medium to be supplied to the third crystallizer, the second cooling medium discharged from the second crystallizer is utilized as a source of the first cooling medium to be supplied to the first crystallizer, and the heating medium discharged from the third crystallizer is utilized as a source of the second cooling medium to be supplied to the second crystallizer. As a result, it becomes possible that the effects of the first and third adjustment operations are exerted for a longer period. In addition, the capacity of the buffer tank is able to be lessened. Further, the operation of the heat source device (refrigerator) can be stabilized and the consumption energy of the heat source device (refrigerator) can be decreased.

As the progress of the respective steps, the temperature T12 of the first cooling medium discharged from the first crystallizer and the temperature T22 of the second cooling medium discharged from the second crystallizer tend to drop, and the temperature T32 of the heating medium discharged from the third crystallizer tends to rise. Therefore, the inequality: T12>T32>T22 could be satisfied during the progress of the respective steps. In such a case, it is preferred that the first cooling medium discharged from the first crystallizer is utilized as a source of the heating medium to be supplied to the third crystallizer, and the heating medium discharged from the third crystallizer is utilized as a source of the first cooling medium to be supplied to the first crystallizer. Or the second cooling medium discharged from the second crystallizer may be utilized as a source of the first cooling medium to be supplied to the first crystallizer, and the heating medium discharged from the third crystallizer may be utilized as a source of the second cooling medium to be supplied to the second crystallizer.

In the case where two or more kinds of the cooling medium or the heating medium are used as shown in FIG. 8, when the cooling medium and the heating medium are mutually utilized such that the cooling medium is utilized as the source of the heating medium and the heating medium is utilized as the source of the cooling medium, it becomes possible that the effects of the first and third adjustment operations are exerted for a longer period, and the capacity of the buffer tank can be lessened. Further, the consumption energy of the heat source device (refrigerator) can be decreased. Therefore, the mutual utilization between the cooling mediums and the mutual utilization between the heating mediums are not essential.

Concerning a rule for utilizing the first cooling medium, the second cooling medium and the heating medium as the mutual sources, it is preferred that the first cooling medium discharged from the first crystallizer 1A is utilized as the source of the heating medium when the temperature T12 of the first cooling medium discharged from the first crystallizer 1A is higher than the temperature T32 of the heating medium discharged from the third crystallizer 1C; and the heating medium discharged from the third crystallizer 1C is utilized as the source of the first or/and second cooling medium when the temperature T32 of the heating medium discharged from the third crystallizer 1C is lower than the temperature T12 of the first cooling medium discharged from the first crystallizer 1A or/and the temperature T22 of the second cooling medium discharged from the second crystallizer 1B. More preferably, the first cooling medium discharged from the first crystallizer 1A is utilized as the source of the heating medium when the temperature T12 of the first cooling medium discharged from the first crystallizer 1A is higher than the temperature T32 of the heating medium discharged from the third crystallizer 1C; and among the heating medium discharged from the third crystallizer 1C and the second cooling medium discharged from the second crystallizer 1B, the higher-temperature heating medium is utilized as the source of the first cooling medium and the lower-temperature heating medium is utilized as the source of the second cooling medium.

Concerning the rule for utilizing the first cooling medium, the second cooling medium and the heating medium as the mutual sources, it is also preferred the cooling medium discharged from the first crystallizer 1A is utilized as the source of the heating medium when the temperature T12 of the cooling medium discharged from the first crystallizer 1A is higher than a predetermined temperature Tb between the temperature T11 of the first cooling medium and the temperature T31 of the heating medium supplied from the refrigerator 7; and the heating medium discharged from the third crystallizer is utilized as the source of the first or/and second cooling medium when the temperature T32 of the heating medium discharged from the third crystallizer 1C is lower than the predetermined temperature Tb between the temperature T11 of the first cooling medium and the temperature T31 of the heating medium supplied from the refrigerator 7. Here, in the case where both the temperature T12 of the first cooling medium to be returned to the refrigerator 7 and the temperature T32 of the heating medium to be returned to the refrigerator 7 are equal to the temperature Tb, the first cooling medium and the heating medium are allowed to be utilized as the either source. The temperature Tb is determined appropriately in accordance with balance of the amounts of utilizing the first cooling medium and the heating medium as the mutual sources. As the temperature Tb, an average value between the temperature T11 of the first cooling medium and the temperature T31 the heating medium, that is (T11+T31)/2, is preferably adopted.

In FIG. 9, after the former part of the crystallizing step in the first crystallizer 1A, the latter part of the crystallizing step in the second crystallizer 1B, and the melting step in the third crystallizer 1C are finished, the latter part of the crystallizing step is conducted in the first crystallizer 1A, the melting step is conducted in the second crystallizer 1B, and the former part of the crystallizing step is conducted in the third crystallizer 1C. Further, after the latter part of the crystallizing step in the first crystallizer 1A, the melting step in the second crystallizer 1B, and the former part of the crystallizing step in the third crystallizer 1C are finished, the melting step is conducted in the first crystallizer 1A, the former part of the crystallizing step is conducted in the second crystallizer 1B, and the latter part of the crystallizing step is conducted in the third crystallizer 1C. In the case where the former part of the crystallizing step, the latter part of the crystallizing step and the melting step are respectively performed in three crystallizers at the same time by rotation like the above, it is preferable that the rule for utilizing the first cooling medium, the second cooling medium and the heating medium as the mutual sources is set as follows, in view of facilitating the operation.

In the case where the former part of the crystallizing step is conducted in the first crystallizer 1A, the preceding step thereof is the melting step, and the first cooling medium discharged from the first crystallizer 1A is utilized as the source of the heating medium without changing the flows of respective mediums through the path 34 from the preceding step. In this case, at the moment soon after the start of the former part of the crystallizing step, extremely high-temperature residual heat remains in the first crystallizer 1A due to the influence of the extremely high-temperature heating medium used in the preceding step thereof, and as a result, the temperature T12 of the first cooling medium discharged from the first crystallizer 1A is likely to be high. Here, the theoretical upper limit of the temperature T12 is equal to the temperature T31. Meanwhile, as the progress of the former part of the crystallizing step, the temperature T12 of the first cooling medium discharged from the first crystallizer 1A drops, and that could theoretically drop to the temperature T11. Hence, when the temperature T12 of the first cooling medium discharged from the first crystallizer 1A is higher than a predetermined temperature Tc between the temperatures T31 and T11 (the temperature Tc is, for example, (T31+T11)/2), the first cooling medium discharged from the first crystallizer 1A is utilized as the source of the heating medium, and when the temperature T12 of the first cooling medium discharged from the first crystallizer 1A is lower than the predetermined temperature Tc (for example, (T31+T11)/2), the first cooling medium discharged from the first crystallizer 1A is utilized as the source the first cooling medium. Here, when the temperature T12 of the first cooling medium is equal to the temperature Tc, the first cooling medium discharged from the first crystallizer 1A is allowed to be utilized as the either source.

In the same manner as described above, in the case where the latter part of the crystallizing step is conducted in the second crystallizer 1B, the preceding step thereof is the former part of the crystallizing step, and hence, when the temperature T22 of the second cooling medium discharged from the second crystallizer 1B is higher than a predetermined temperature Td between the temperatures T11 and T21 (the temperature Td is, for example, (T11+T21)/2), the second cooling medium discharged from the second crystallizer 1B is utilized as the source of the first cooling medium, and when the temperature T22 of the second cooling medium discharged from the second crystallizer 1B is lower than the predetermined temperature Td (for example, (T11+T21)/2), the second cooling medium discharged from the second crystallizer 1B is utilized as the source the second cooling medium. Here, when the temperature T22 of the second cooling medium is equal to the temperature Td, the second cooling medium discharged from the second crystallizer 1B is allowed to be utilized as the either source.

In the case where the melting step is conducted in the third crystallizer 1C, the preceding step thereof is the latter part of the crystallizing step, and at the beginning of the melting step, the heating medium discharged from the third crystallizer 1C is utilized as the source of the second cooling medium without changing the flows of respective mediums through the path 34 from the preceding step. In this case, at the moment soon after the start of the melting step, extremely low-temperature residual heat remains in the third crystallizer 1C due to the influence of the extremely low-temperature second cooling medium used in the preceding step thereof, and as a result, the temperature T32 of the heating medium discharged from the third crystallizer 1C is likely to be low. Here, the theoretical lower limit of the temperature T32 is equal to the temperature T21. Meanwhile, the theoretical upper limit of the temperature T32 is equal to the temperature T31. Hence, when the temperature T32 of the heating medium discharged from the third crystallizer 1C is lower than a predetermined temperature Te between the temperatures T21 and T31 (the temperature Te is, for example, (T21+T31)/2), the heating medium discharged from the third crystallizer 1C is utilized as the source of the second cooling medium, and when the temperature T32 of the heating medium discharged from the third crystallizer 1C is higher than the predetermined temperature Te (for example, (T21+T31)/2), the heating medium discharged from the third crystallizer 1C is utilized as the source the heating medium. Here, when the temperature T32 of the heating medium is equal to the temperature Te, the heating medium discharged from the third crystallizer 1C is allowed to be utilized as the either source.

Thus, in the above case, a part or all of the first cooling medium discharged from the first crystallizer is utilized as the source of the heating medium, a part or all of the second cooling medium discharged from the second crystallizer is utilized as the source of the first cooling medium, and a part or all of the heating medium discharged from the third crystallizer is utilized as the source of the second cooling medium. And, when the rule for utilizing the first cooling medium, the second cooling medium and the heating medium as the mutual sources is set as the above, the operation for switching the path 34 becomes easy.

In the case where the process for producing (meth)acrylic acid of the present invention comprises the crystallizing step, it is preferred that the producing process of the present invention further comprises the step of obtaining the crude (meth)acrylic acid solution.

The step of obtaining the crude (meth)acrylic acid solution preferably includes a gas-phase catalytic oxidation step of producing (meth)acrylic acid-containing gas from a (meth) acrylic acid production raw material by gas-phase catalytic oxidation and a collection step of collecting the (meth)acrylic acid-containing gas with a liquid medium. Further, for the purpose of increasing (meth)acrylic acid content in the (meth) acrylic acid solution obtained by the collection step, a purification step may be provided after the collection step.

In the gas-phase catalytic oxidation step, propane, propylene, (meth)acrolein, isobutylene, or the like is used as the (meth)acrylic acid production raw material, and the (meth) acrylic acid production raw material undergoes gas-phase catalytic oxidation by molecular oxygen to produce the (meth)acrylic acid-containing gas. The gas-phase catalytic oxidation is preferably carried out using a conventionally-known oxidation catalyst.

In the collection step, the (meth)acrylic acid-containing gas obtained by the gas-phase catalytic oxidation step is collected with a liquid medium in a collection column to give the (meth)acrylic acid solution. Examples of the liquid medium include water, (meth)acrylic acid-containing water, a high boiling point solvent (e.g. diphenyl ether, biphenyl and the like), and the like. In the present invention, the (meth)acrylic acid solution obtained by the collection step may be subjected to the crystallizing step as the crude (meth)acrylic acid solution.

In the case where the (meth)acrylic acid content in the (meth)acrylic acid solution obtained by the collection step is low, the purification step may be provided after the collection step, and the (meth)acrylic acid solution obtained by the collection step may be purified by distillation, diffusion or the like to give the crude (meth)acrylic acid solution to be subjected to the crystallizing step.

In the case where the process for producing (meth)acrylic acid of the present invention comprises the melting step but does not comprise the crystallizing step, it is preferred that the producing process of the present invention further comprises the step of crystallizing (meth)acrylic acid by any crystallizing method.

In the process for producing (meth)acrylic acid of the present invention, the following steps can be also employed: the steps of producing (meth)acrolein by dehydrating glycerin or 2-methylglycerin and obtaining the crude (meth)acrylic acid solution by gas-phase oxidation of the (meth)acrolein; or the steps of producing hydroxypropionic acid, which is hereinafter referred to as HP, or 2-methyl-3-hydroxypropionic acid from a biomass and the like of a renewable source and obtaining the crude (meth)acrylic acid solution by dehydrating the HP. A process for obtaining crude acrylic acid by dehydration and oxidation of glycerin and a process for producing the HP and obtaining crude acrylic acid by dehydration of the HP are described below.

In the process for producing acrolein, glycerin is dehydrated in the presence of a catalyst to produce acrolein, and examples of the catalyst include a solid catalyst having an acid property. As a solid acid catalyst having an acid property, compounds having a solid acid can be used, and examples of the solid acid catalyst include (a) a crystalline metallosilicate, (b) a metal oxide, (c) a clay mineral, (d) a substance in which a mineral acid is supported on an inorganic carrier such as α-alumina, silica, zirconium oxide, titanium oxide or the like, (e) a metal salt of phosphoric acid, sulfuric acid or the like and a substance in which the metal salt is supported on an inorganic carrier such as α-alumina, silica, zirconium oxide, titanium oxide or the like.

(a) Examples of the crystalline metallosilicate include a compound which contains one or more kind(s) of T atoms selected from the group consisting of Al, B, Fe and Ga, and has a crystalline structure such as LTA, CHA, FER, MFI, MOR, BEA or MTW. (b) Examples of the metal oxide include single metal oxides such as $Al_2O_3$, $TiO_2$, $ZrO_2$, $SnO_2$ and $V_2O_5$, and complex oxides such as $SiO_2$—$Al_2O_3$, $SiO_2$—$TiO_2$, $TiO_2$—$WO_3$ and $WO_3$—$ZrO_2$. (c) Examples of the clay mineral include bentonite, kaolin and montmorillonite. (d) Examples of the substance in which a mineral acid is supported on an inorganic carrier include a substance in which phosphoric acid, sulfuric acid or the like is supported on alumina, silica, zirconia or the like. (e) Examples of the phosphoric acid and the sulfuric acid include $MgSO_4$, $Al_2(SO_4)_3$, $K_2SO_4$, $AlPO_4$, $BPO_4$, $Zr_3(PO_4)_4$.

Specifically, a solid acid disclosed in International Publications WO 2006/087083 and WO 2006/087084, that is zirconium oxide supporting phosphoric acid, sulfuric acid or tungsten oxide, may be used.

Among them, a highly stable solid catalyst is preferable, since it can be put in oxidation or reduction atmosphere of high temperature during the dehydration or a regeneration treatment. Specifically, crystalline metallosilicates, metal oxides, clay minerals and the like are preferred; and HZSM-5, which contains Al as the T atom and has a MFI structure, is preferred as the crystalline metallosilicate, and a crystalline phosphate compound is preferred and aluminum phosphate is particularly preferred as the metal oxide.

Concerning acid strength of HZSM-5, it is known that HZSM-5 has a strong acidity having peaks about −9 and −16 in Hammett acid strength parameter $H_0$ (refer to the document: Kenji Hashimoto et al., Shokubai, vol. 29, No. 6, pp. 406-409, 1987), and it is known that acid strength of aluminum phosphate changes depending on a preparing method thereof and a crystalline structure, and aluminum phosphate has weak solid acidity of +1.5 to +4.8 in Hammett acid strength parameter $H_0$ (refer to the document: Kiyoko Sakamoto et al., Nippon Kagaku Kaishi, 1995(9), pp. 681-688).

In the process for producing acrolein, acrolein is produced by a gas-phase dehydration reaction that is conducted by bringing a reaction gas containing glycerin into contact with a catalyst in any reactor selected from, for example, a fixed-bed reactor, a fluidized-bed reactor, a moving-bed reactor, and the like. However, not only the gas-phase dehydration reaction that is conducted by bringing the reaction gas containing glycerin into contact with a catalyst, but also liquid-phase dehydration reaction that is conducted by bringing a glycerin solution into contact with a catalyst can be employed. In the latter case, the liquid-phase dehydration reaction can be carried out by conventionally-known various methods such as a method of using a fixed-bed reactor and a distillation column in combination, a method of using a stirring vessel and a distillation column in combination, a method of using a single-stage stirring vessel, a method of using a multistage stirring vessel, a method of using a multistage distillation column, and combinations thereof. These methods may be conducted either batch-wise or continuously, and generally conducted continuously.

A process for producing acrolein that utilizes the gas-phase dehydration reaction, which is excellent in industrial productivity of acrolein, is hereinafter explained, as an example.

The reaction gas may be a gas consisting of only glycerin or further contain an inert gas which is inactive against the dehydration reaction of glycerin so that a glycerin concentration in the reaction gas is adjusted. Examples of the inert gas include, for example, steam, nitrogen, carbon dioxide gas, and air. The glycerin concentration in the reaction gas is generally in the range of 0.1 mol % to 100 mol %, preferably 1 mol % or more, and more preferably 5 mol % or more for economically producing acrolein in high efficiency.

As the catalyst, a catalyst for dehydrating glycerin that shows high acrolein selectivity is preferably used, and using such a catalyst makes it possible to produce acrolein in high yield even when the reaction gas is introduced at a high flow rate. A flow rate of the reaction gas, a gas space velocity per unit volume of the catalyst (GHSV), is generally in the range of 50 $h^{-1}$ to 20000 $h^{-1}$, preferably 10000 $h^{-1}$ or lower, and more preferably 4000 $h^{-1}$ or lower for economically producing acrolein in high efficiency.

Reaction temperature is generally in the range of 200° C. to 500° C., preferably in the range of 250° C. to 450° C., and more preferably in the range of 300° C. to 400° C.

A pressure of the reaction gas is not particularly limited as long as it is in the range where glycerin does not become condensed, and is generally in the range of 0.001 MPa to 1 MPa, preferably in the range of 0.01 MPa to 0.5 MPa, and more preferably 0.3 MPa or lower.

When the dehydration reaction of acrolein is continuously conducted, carbonaceous matters may be deposited on the surface of the catalyst, resulting in decreasing the activity of the catalyst. Specifically, selectivity of acrolein is lowered and selectivity of propionaldehyde is enhanced. In such a case, when a regeneration treatment in which the catalyst is brought into contact with a regeneration gas at high temperature is conducted, carbonaceous matters deposited on the surface of the catalyst can be removed, thereby regenerating the activity of the catalyst. Examples of the regeneration gas include, for example, oxidative gases such as oxygen and air which contains oxygen. The regeneration gas may further contain an inert gas which is inactive against the regeneration treatment, such as nitrogen, carbon dioxide and steam, if needed. In the case where there is a risk of abrupt heat generation due to contact of the catalyst with oxygen, it is recommended that the inert gas is contained in the regeneration gas for suppressing the abrupt heat generation. Temperature required for the regeneration treatment is not particularly limited as long as the carbonaceous matters can be removed without occurring heat deterioration of the catalyst, and is preferably equal to or lower than calcination temperature in preparing the catalyst.

Crude acrolein prepared by the dehydration reaction of glycerin contains by-products. Therefore, it is preferred that the thus obtained crude acrolein is subjected to purification. Examples of the by-product include, for example, phenol, 1-hydroxyacetone, and allyl alcohol in addition to propionaldehyde. In the purification of the crude acrolein, phenol and/or 1-hydroxyacton are mainly removed. When these by-products are removed, yield of acrylic acid is enhanced in producing acrylic acid from acrolein. Especially, product amount of acetic acid can be reduced when 1-hydroxyaceton is removed.

In consideration of enhancing the yield of acrylic acid, it is considered to be preferable that a larger amount of phenol and/or 1-hydroxyacton is removed. Therefore, a mass ratio Ph/A of a mass of acrolein (A) and a mass of phenol (Ph) after the purification and a mass ratio H/A of a mass of acrolein (A) and a mass of 1-hydroxyacetone (H) after the purification are respectively preferably 0.020 or less, more preferably 0.010 or less, and further more preferably 0.005 or less. Meanwhile, when a further larger amount of phenol and/or 1-hydroxyacton is removed, loss of acrolein may be increased or the purification of acrolein may be complicated. Taking these facts into consideration, the mass ratios Ph/A and H/A are preferably $1 \times 10^{-9}$ or more, more preferably $1 \times 10^{-7}$ or more, and further more preferably $1 \times 10^{-5}$ or more.

Boiling points of acrolein, phenol and 1-hydroxyacetone are about 53° C., about 182° C. and about 146° C., respectively. By utilizing the differences between theses boiling points, phenol and/or 1-hydroxyacetone can be removed from the crude acrolein. Methods for that include, for example, a method of fractional-distilling acrolein having a lower boiling point than removal objectives by treating the liquid crude acrolein with a distillation column, a method of condensing removal objectives having higher boiling points than acrolein by treating the gaseous crude acrolein with a condensation column, and a method of vaporizing acrolein having a lower boiling point than removal objectives by blowing a gas into the crude acrolein introduced into a diffusion column.

In addition, melting points of acrolein, phenol and 1-hydroxyacetone are about −87° C., about 43° C. and about −17° C., respectively. By utilizing the differences between theses melting points, phenol and/or 1-hydroxyacetone can be removed from the crude acrolein. Method for that include, for example, a method of removing crystals of phenol and/or 1-hydroxyacetone by cooling the crude acrolein.

Propionaldehyde has a boiling point of about 48° C. and a melting point of about −81° C., and therefore, it is possible to remove propionaldehyde from the crude acrolein by utilizing the difference of the boiling or melting points between propionaldehyde and acrolein. However, since the both differences of the boiling point and the melting point between propionaldehyde and acrolein are small, loss of acrolein may possibly be increased. Therefore, propionaldehyde is preferably treated along with acrolein, a precursor of acrylic acid, without being separated from acrolein.

In the case of using glycerin derived from biodiesel as the raw material, the obtained crude acrolein may be used without being purified; however, it contains impurities such as phenol, 1-hydroxyacetone, methoxyacetone, 3-methoxypropanal and the like, which cause deterioration of catalyst activity, decrease of yield, or production of byproducts such as formic acid, acetic acid, propionic acid, pyruvic acid, 3-methoxypropionic acid in acrylic acid, and hence, the crude acrolein may be purified to be used. The purification can be conducted by a conventionally-known method, and examples of the purification include a method of distilling a condensed liquid of the reaction composition or a collection liquid obtained by using a collection solvent, and a method of using a purification apparatus provided with a collection column and a diffusion column, which is disclosed in Japanese Unexamined Patent Application Publication No. 2008-115103. In the case where the crude acrolein is not purified, impurities in acrylic acid may be removed by purifying acrylic acid in the subsequent step. In view of simplifying the process and lowering production cost, it is preferred that the crude acrolein is not purified to be used.

Acrylic acid can be produced by oxidizing acrolein obtained in the above process for producing acrolein. For producing acrylic acid, it is preferred that a gas containing acrolein, which may be hereinafter referred to as a "acrolein-containing gas", is brought into coexistence with a catalyst for oxidizing acrolein, which may be hereinafter referred to as a "acrolein-oxidizing catalyst", in any oxidation reactor selected from a fixed-bed reactor, a moving-bed reactor, a fluidized-bed reactor and the like at a temperature in the range of 200° C. to 400° C., thereby conducting gas-phase oxidation of acrolein. The oxidation of acrolein may be accompanied by production of propionic acid from propionaldehyde.

As the acrolein-oxidizing catalyst, any conventionally-known catalysts for oxidizing acrolein can be employed that can be used for producing acrylic acid by gas-phase catalytic oxidation of acrolein with molecular oxygen or molecular oxygen-containing gas; and examples of the acrolein-oxidizing catalyst include, for example, a mixture or a complex oxide of metal oxides such as iron oxide, molybdenum oxide, titanium oxide, vanadium oxide, tungsten oxide, antimony oxide, tin oxide, copper oxide. Among these catalysts, a molybdenum-vanadium catalyst which containing molybdenum and vanadium as essential components is particularly preferable. The acrolein-oxidizing catalyst may be a supported catalyst in which a mixture or a complex oxide of metal oxides described above is supported on a carrier (e.g. an inorganic oxide such as silica, alumina, zirconia, a complex oxide thereof, and an inorganic substance such as silicon carbide).

Concerning the feed amount of oxygen relative to the acrolein-containing gas used in the production of acrylic acid, the upper limit thereof is needed to be appropriately set, since the excess amount of oxygen may cause an explosion hazard due to combustion of acrolein.

By the gas-phase catalytic oxidation of acrolein, a gaseous substance containing crude acrylic acid is obtained. In a collection step, the gaseous substance is liquefied by cold condensation, solvent collection or the like, thereby obtaining a crude acrylic acid solution. The thus obtained crude acrylic acid can be subjected to the crystallizing step of the present invention.

A process for producing acrylic acid from a biomass or the like of a renewable source is hereinafter described. There is no direct route to produce acrylic acid from a biomass, however, acrylic acid can be produced rather easily by dehydrating hydroxycarboxylic acid such as 3-hydroxypropionic acid (hereinafter may be referred to as 3HP), which can be prepared by fermentation of sugar available from decomposition of lactic acid (hereinafter may be referred to as 2HP), cellulose or the like, which are natural substances and compassable easily. Acrylic acid can be also prepared by dehydrating a salt of hydroxycarboxylic acid.

Hydroxycarboxylic acid and/or a salt thereof is available from various resources. Biological resources which are recyclable as a carbon source are preferably used in view of global warming and protection of environment, and 2-hydroxypropionic available from natural products and 2-hydrocypropionic acid or 3-hydroxypropionic acid prepared by fermentation of sugar available from decomposition of cellulose or the like can be used.

An aqueous solution of 2-hydroxypropionic acid can be prepared by known-methods such as, for example, fermentation using *lactobacillus* described in the document: Advance in Applied Microbiology, vol. 42, pp. 45-95 (1996), and fermentation using fungi described in the document: Enzyme and Microbial Technology, vol. 26, pp. 87-107 (2000).

An aqueous solution of 3-hydroxypropionic acid can be also prepared by known-methods such as, for example, fermentation of glucose as a carbon source using transgenic *Escherichia coli* beta-alanine aminotransferase derived from *Streptomyces griseus* ATCC21897 described in the document: International Publication WO 2008/027742, and fermentation of glycerin as a carbon source using *Escherichia coli* to which glycerin dehydratase derived from *Klebsiella pneumoniae* and aldehyde oxidase derived from *Escherichia coli* are introduced described in the document: International Publication WO 2001/016346. Any bacteria or modified bacteria can be used for the fermentations, as long as the methods described in the above documents, that show examples of preparing methods of 3-hydroxypropionic acid aqueous solution, are employed; and 3-hydroxypropionic acid aqueous solution prepared by fermentation of various carbon sources using an organism capable of forming 3-hydroxypropionic acid can be used in the process of the present invention. Further, 3-hydroxypropionic acid aqueous solution prepared by contacting between sugar as a raw material and an organism without fermenting can be also converted into acrylic acid by the process of the present invention. As a manner of contacting between sugar and an organism, the embodiment of conducting reaction using a microorganism or a processed microorganism in the presence of sugar used as a raw material is included. Examples of the processed microorganism include a microorganism treated with acetone, toluene or the like, a destroyed microorganism, a lyophilized microorganism, a fractured microorganism, a cell-free extract of a fractured microorganism, and a crude enzyme liquid or a purified enzyme obtained by extracting an enzyme therefrom. Furthermore, 3-hydroxypropionic acid aqueous solution prepared by reaction using a microorganism fixed on a carrier by a common means, a processed material thereof, or an enzyme can be also used.

For producing crude acrylic acid by dehydrating hydroxycarboxylic acid, known-methods can be employed. For example, Japanese Unexamined Laid-open Patent Application Publication No. 2005-521718 discloses a method for producing unsaturated carboxylic acid or salt thereof where an aqueous solution or a solution of 2,3-hydroxycarboxylic acid (2HP and 3HP) or salt thereof prepared by fermentation is heated in the presence or the absence of a catalyst, thereby dehydrated. International Publication WO 2005/095320 discloses a method for producing 2,3-unsaturated carboxylic acid where an aqueous solution of 2,3-hydroxycarboxylic acid is fed to a place in which an inactive ceramic or an acidic or basic solid catalyst is held, and heated. International Publication WO 2007/106100 discloses a method for producing a reaction product containing 2,3-unsaturated carboxylic acid compound where a composition containing 3-hydroxycarbonyl compound is fed to a reactor in a substantive liquid form and converted in the reactor. In this method, an acid catalyst, a basic catalyst or the like is used in the reactor.

The thus obtained acrylic acid is a liquid substance or a gaseous substance containing crude acrylic acid. The liquid substance can be used as-is as the crude acrylic acid solution in the present invention. The gaseous substance is liquefied by cold condensation, solvent collection or the like in the collection step, whereby a crude acrylic acid solution can be obtained, and the crude acrylic acid solution can used in the crystallizing step of the present invention. In addition, since hydroxypropionic acid prepared by fermentation and crude acrylic acid prepared by dehydrating hydroxypropionic acid which has been prepared by fermentation contain impurities such as organic acids other than acrylic acid, it is quite effective to purify the crude acrylic acid by a crystallization operation of the present invention for obtaining acrylic acid with high-purity.

(Meth)acrylic acid produced by the producing process of the present invention is excellent in quality stability, and hence, when the (meth)acrylic acid is used as a monomer for producing a hydrophilic resin such as an absorbent resin and a water-soluble resin, the polymerization reaction is easily controlled and quality of the hydrophilic resin is stabilized, thereby improving various properties such as absorption performance and dispersibility of inorganic substances. Especially, since acrylic acid produced by the producing process of the present invention is excellent in quality stability and controllability in the polymerization reaction, it is quite useful as a raw material for producing an absorbent resin having high absorbency and high quality.

Definitions concerning the absorbent resin of the present invention and preferable embodiments for production thereof are hereinafter explained.

(1) "Absorbent Resin"

The term "absorbent resin" in the present invention means a water-swellable and water-insolble polymer gelling agent. The term "water-swellable" means that CRC (absorption ratio under non-pressure) specified in ERT 441.2-02 is generally 5 g/g or more, and the term "water-insoluble" means Ext (water solubles) specified in ERT 470.2-02 is generally 0 mass % or more and 50 mass % or less.

The absorbent resin can be designed appropriately depending on the intended use thereof and is not particularly limited; however, it is preferably a hydrophilic cross-linked polymer prepared by cross-linking polymerization of unsaturated monomer(s) having a carboxyl group. The absorbent resin is not limited to a form where whole amount (100%) is a polymer, and may include additives and the like in a range to maintain the above properties.

In the present invention, it means an absorbent resin which is composed principally of acrylic acid and/or a salt thereof (hereinafter referred to as "acrylic acid (salt)" as a repeating unit and may contain a graft constituent as needed. Specifically, the absorbent resin contains acrylic acid (salt) generally in 50 mol % to 100 mol %, preferably in 70 mol % to 100 mol %, more preferably in 90 mol % to 100 mol %, and particularly preferably substantially in 100 mol %, among the total amount of monomer(s) used in the polymerization except a cross-linking agent.

(2) "EDANA" and "ERT"

The term "EDANA" is an abbreviation for European Disposables and Nonwovens Association, and the term "ERT" is an abbreviation for the measurement method (EDANA Recommended Test Methods) for the absorbent resin of an European standard (nearly a world standard). In the present invention, unless otherwise specified, the ERT original (known document: revised in 2002) is referred to in measuring properties of the absorbent resin.

(a) "CRC" (ERT 441.2-02)

The term "CRC" is an abbreviation for Centrifuge Retention Capacity and means an absorption ratio under non-pressure (hereinafter may be referred to as an "absorption ratio"). Specifically, it means an absorption ratio (unit: g/g) measured by having an absorbent resin swell freely in 0.9 mass % sodium chloride aqueous solution for 30 minutes and dewatering using a centrifuge.

The absorbent resin obtained in the present invention preferably has the CRC of 20 g/g or more and 100 g/g or less, more preferably 25 g/g or more and 50 g/g or less, and further more preferably 27 g/g or more and 45 g/g or less.

(b) "AAP" (ERT 442.2-02)

The term "AAP" is an abbreviation for Absorption Against Pressure and means an absorption ratio under pressure. Specifically, it means an absorption ratio (unit: g/g) measured by having an absorbent resin swell in 0.9 mass % sodium chloride aqueous solution under a pressure of 2.06 kPa for 1 hour; however, in the present invention, it means an absorption ratio (unit: g/g) measured in the condition of under a pressure of 4.83 kPa for 1 hour.

The absorbent resin obtained in the present invention preferably has the AAP of 20 g/g or more and 30 g/g or less, and more preferably 22 g/g or more and 30 g/g or less.

(c) "Ext" (ERT 470.2-02)

The term "Ext" is an abbreviation for Extractables and means water solubles (a content of water-soluble component). Specifically, it is a value (unit: mass %) of a dissolved amount of a polymer, that is measured by pH titration, when 1 g of an absorbent resin is fed to 200 g of 0.9 mass % sodium chloride aqueous solution and stirred at 500 rpm for 16 hours. The absorbent resin obtained in the present invention preferably has the Ext of 0 g/g or more and 30 g/g or less, and more preferably 0 g/g or more and 20 g/g or less.

(d) "FSC" (ERT 440.2-02)

The term "FSC" is an abbreviation for Free Swell Capacity and means a rate of freely-swelling. Specifically, it means an absorption ratio (unit: g/g) measured by having 0.20 g of an absorbent resin swell freely in 0.9 mass % sodium chloride aqueous solution for 30 minutes and not dewatering using a centrifuge.

(e) "Residual Monomers" (ERT 410.2-02)

The term "Residual Monomers (RM)" is a residual amount of monomer(s) in an absorbent resin. Specifically, it means a value (unit: ppm) is measured by a high-performance liquid chromatography, when 1.0 g of an absorbent resin is fed to 200 cm$^3$ of the 0.9 mass % sodium chloride aqueous solution and stirred at 500 rpm for 1 hour. The absorbent resin obtained in the present invention preferably has the RM of 1000 ppm or less, and more preferably 500 ppm or less.

(f) "PSD" (ERT 420.2-02)

The term "PSD" is an abbreviation for Particle Size Distribution and means a particle size distribution measured by a sieve classification. A weight average particle diameter (D50) and a particle diameter distribution width are measured by similar methods described in "(1) Average Particle Diameter and Distribution of Particle Diameter" of page 7, lines 25-43 in European Patent Publication No. 0349240.

(3) "Liquid Permeability"

The term "liquid permeability" means a liquid flow between swollen gel particles under pressure or non-pressure. As typical measurement methods of the "liquid permeability", SFC (Saline Flow Conductivity) and GBP (Gel Bed Permeability) are indicated.

"SFC (Saline Flow Conductivity)" means permeability of 0.69 mass % saline through an absorbent resin under a load of 0.3 psi. It is measured according to the SFC test method described in U.S. Pat. No. 5,669,894. The unit thereof is "$cm^3*s*10^{-7}/g$".

"GBP" means permeability of 0.69 mass % saline through an absorbent resin under load or freely-swelling. It is measured according to the GBP test method described in International Publication WO 2005/016393.

The absorbent resin obtained in the present invention preferably has the SFC of 1 or more, and more preferably 5 or more.

(4) Preferred Embodiments for Production

Acrylic acid and/or a salt thereof produced according to the process of the present invention is used as a main component of monomer(s), and polymerized and cross-linked using a radical polymerization initiator of about 0.001 mol % of more and 2 mol % or less and a cross-linking agent of about 0.01 mol % or more and 5 mol % or less, respectively relative to the acrylic acid and/or a salt thereof, and then dried and pulverized, thereby obtaining the absorbent resin.

Preferred producing methods in terms of higher productivity of the absorbent resin are described in, for example, U.S. Pat. Nos. 6,867,269, 6,906,159, 7,091,253 and International Publications WO 01/038402 and WO 2006/034806.

A method for polymerizing acrylic acid obtained by the process of the present invention is not particularly limited; and a continuous belt-type polymerization disclosed in U.S. Pat. Nos. 4,893,999, 6,241,928, U.S. Patent Application Publication No. 2005/215734 and the like, a continuous kneader-type polymerization and a batch kneader-type polymerization disclosed in U.S. Pat. Nos. 6,987,151, 6,710,141 and the like, are preferably employed.

The thus obtained polymer is preferably converted into a particulate absorbent resin by the producing method disclosed in U.S. Pat. Nos. 4,920,202, 5,264,495, 5,275,773, 6,207,796, 6,164,455, 6,207,796, 6,291,636, 6,875,511 or the like.

Further, the absorbent resin is preferably cross-linked on the surface thereof, depending on the purpose or application thereof, especially in the case of applying to sanitary articles. As concrete embodiments, producing methods disclosed in European Patent Publication Nos. 0349240, 0605150, 0450923, 0812873, 0450924, 0668080, Japanese Unexamined Laid-open Patent Application Publication Nos. 7-242709, 7-224304, U.S. Pat. Nos. 5,409,771, 5,597,873, 5,385,983, 5,610,220, 5,633,316, 5,674,633, 5,462,972, International Publications WO 99/42494, WO 99/43720, WO 99/42496, and the like are preferred.

The above-described publications are incorporated into the present specification by reference.

[2. A Crystallization System]

A crystallization system of the present invention is hereinafter explained. The crystallization system of the present invention comprises a crystallizer, a heat source device and a buffer tank. In the case where the crystallizer is used for conducting a crystallizing operation, the crystallization system of the present invention comprises the crystallizer, a heat source device and a first buffer tank. In the case where the crystallizer is used for conducting a melting operation, the crystallization system of the present invention comprises the crystallizer, a heat source device and a second buffer tank.

The crystallizer used in the crystallization system of the present invention is provided with a heat-transfer surface and the interior of the crystallizer is partitioned into a medium-present part and a crystal-present part partitioned by the heat-transfer surface. In the medium-present part, a cooling medium or a heating medium is present, and in the crystal-present part, a solution to be crystallized and/or a crystal is present. In the present invention, a crude (meth)acrylic acid solution and/or a (meth)acrylic acid crystal is preferably present in the crystal-present part. No particular limitation is placed on the heat-transfer surface, as long as the heat-transfer surface partitions the crystallizer into two parts, namely, the medium-present part and the crystal-present part, and heat is exchanged via the heat-transfer surface.

As the crystallizer provided with the heat-transfer surface, an apparatus used as a heat exchanger generally can be employed, and heat exchangers exemplified in the above can be employed.

In the crystallizer, when the cooling medium is present in the medium-present part and the solution to be crystallized is present in the crystal-present part, the solution to be crystallized is cooled via the heat-transfer surface, thereby generating a crystal. Also, when the heating medium is present in the medium-present part and a crystal is present in the crystal-present part, the crystal is heated via the heat-transfer surface to be melted, thereby obtaining a melt of the crystal.

The medium-present part is provided with an inlet (a medium supply-port) through which the cooling medium and/or the heating medium is supplied and an outlet (a medium discharge-port) through which the cooling medium and/or the heating medium is discharged. The crystal-present part is provided with an inlet through which the solution to be crystallized is supplied and an outlet through which the solution to be crystallized and/or the melt of the crystal is discharged.

The heat source device used in the crystallization system of the present invention is not particularly limited as long as it is capable of cooling the cooling medium and/or heating the heating medium, and heat source devices exemplified in the above can be employed. As the heat source device, a refrigerator which cools the cooling medium and heats the heating medium may be employed.

In the case where the heat source device is an apparatus which cools the cooling medium, the heat source device is provided with a cooling medium-supply port through which the cooling medium is supplied and a cooling medium-return port through which the cooling medium is returned. The cooling medium-supply port of the heat source device is connected to the inlet of the medium-present part, and the cooling medium is discharged from the heat source device through the cooling medium-supply port and supplied to the medium-present part of the crystallizer. The cooling medium-return port of the heat source device is connected to the outlet of the medium-present part of the crystallizer, and the cooling medium discharged from the medium-present part of the crystallizer is returned to the heat source device through the cooling medium-return port.

In the case where the heat source device is an apparatus which heats the heating medium, the heat source device is provided with a heating medium-supply port through which the heating medium is supplied and a heating medium-return port through which the heating medium is returned. The heating medium-supply port of the heat source device is connected to the inlet of the medium-present part, and the heating medium is discharged from the heat source device through the heating medium-supply port and supplied to the medium-present part of the crystallizer. The heating medium-return port of the heat source device is connected to the outlet of the medium-present part of the crystallizer, and the heating medium discharged from the medium-present part of the crystallizer is returned to the heat source device through the heating medium-return port.

The buffer tank used in the crystallization system of the present invention is provided with two openings, namely, an upper opening and a lower opening. No limitation is placed on the buffer tank as long as the cooling medium or the heating medium can be stored in the buffer tank, and any particular structures may not be installed in the buffer tank.

The buffer tank retains the cooling medium or the heating medium having a temperature gradient in a vertical direction such that an upper part is high-temperature and a lower part is low-temperature. In order that the cooling medium or the heating medium is retained in the buffer tank so as to form the temperature gradient in the vertical direction such that the upper part is high-temperature and the lower part is low-temperature, it is only necessary to feed the cooling or heating medium having high temperature into the buffer tank through the upper opening and feed the cooling or heating medium having low temperature into the buffer tank through the lower opening, whereby the temperature gradient in the vertical direction is naturally formed in the cooling medium or the heating medium retained in the buffer tank.

The shape of the buffer tank is not particularly limited, and practical cylindrical shape such as circular cylinder and multangular cylinder is preferable. Distance between the upper opening and the lower opening of the buffer tank is preferably equal to or more than a maximum cross-section length of the buffer tank, more preferably more than twice the maximum cross-section length, and further more preferably more than four times the maximum cross-section length. Thus, the distance between the upper opening and the lower opening of the buffer tank is at least equal to a width of the buffer tank or more, and when the buffer tank has such a shape, the temperature gradient in the vertical direction is easily formed in the cooling medium or the heating medium retained in the buffer tank.

Concerning the maximum cross-section length of the buffer tank, for example, in the case where the shape of the buffer tank is a circular cylinder, the maximum cross-section length of the buffer tank corresponds to the diameter of the circular bottom, and in the case where the shape of the buffer tank has a rectangular cylinder, the maximum cross-section length of the buffer tank corresponds to the length between the opposing corners of the rectangular bottom. In the case where the shape of the buffer tank is a cylinder except the lower part and the shape of the lower part is a pyramid or a cone narrowing downward, the maximum cross-section length of the buffer tank corresponds to the maximum cross-section length of the part having a cylindrical shape. In the case where the buffer tank has such a shape that the intermediate part in the vertical direction thereof widen, the maximum cross-section length of the buffer tank corresponds to the maximum cross-section length at the widest part of the intermediate part.

The upper opening and the lower opening are arranged in the buffer tank so that the upper opening is located above the lower opening. When the respective openings are arranged in this manner, the cooling medium or the heating medium is retained in the buffer tank so that a fluid level thereof is positioned at the upper opening.

As the upper opening and the lower opening, for example, openings may be formed on the outer surface of the buffer tank, or pipes opening into the interior of the buffer tank may be installed to the buffer tank. Preferably, as the upper opening, a pipe which opens upward in the interior of the buffer tank is installed to the buffer tank. As the lower opening, an opening is preferably formed at the bottom of the buffer tank. Both the upper opening and the lower opening are provided preferably such that the openings are located at the center of the cross-section of the buffer tank. By providing the upper opening and the lower opening in this manner, the temperature gradient of the cooling or heating medium retained in the buffer tank is easily maintained when the cooling or heating medium is inflowed or outflowed through the respective openings.

Flow paths connecting the crystallizer, the heat source device and the buffer tank are hereinafter explained referring to FIGS. 1 and 4.

FIG. 1 shows paths for utilizing the first buffer tank as the buffer tank, and shows a crystallization system where crystallizing is performed using a cooling medium. In the case of using a cooling medium, the crystallization system of the present invention comprises a crystallizer 1, a heat source device 4 and a first buffer tank 5. A cooling medium-supply port 4a of the heat source device 4 is connected to an inlet 2a of a medium-present part 2 of the crystallizer 1, and an outlet 2b of the medium-present part 2 of the crystallizer 1 is connected to a cooling medium-return port 4b of the heat source device 4. As a result, a circulation path for the cooling medium is formed between the crystallizer 1 and the heat source device 4. The cooling medium supplied to the medium-present part 2 of the crystallizer 1 from the heat source device 4 is heat-exchanged in the crystallizer 1, and then discharged from the medium-present part 2 of the crystallizer 1 and returned to the heat source device 4. When the cooling medium is heat-exchanged in the crystallizer 1, a crystal is generated within a crystal-present part 3 of the crystallizer 1. The cooling medium which has been returned to the heat source device 4 is cooled by the heat source device 4 and discharged again from the heat source device 4 through the cooling medium-supply port 4a.

The first buffer tank 5 is provided with an upper opening 5a connected to the outlet 2b of the medium-present part 2 of the crystallizer 1 and the cooling medium-return port 4b of the heat source device 4. As a result, a path for feeding the cooling medium discharged from the crystallizer 1 to the upper opening 5a of the first buffer tank 5, and a path for returning the cooling medium discharged from the upper opening 5a of the first buffer tank 5 to the heat source device 4, are formed.

The first buffer tank 5 is provided with a lower opening 5b connected to the cooling medium-supply port 4a of the heat source device 4 and/or the outlet 2b of the medium-present part 2 of the crystallizer 1, and the cooling medium-return port 4b of the heat source device 4. As a result, a path for feeding the cooling medium supplied from the heat source device 4 and/or the cooling medium discharged from the crystallizer 1 to the lower opening 5b of the first buffer tank 5, and a path for returning the cooling medium discharged from the lower opening 5b of the first buffer tank 5 to the heat source device 4, are formed.

FIG. 4 shows paths for utilizing the second buffer tank as the buffer tank, and shows a crystallization system where melting is performed using a heating medium. In the case of using a heating medium, the crystallization system of the present invention comprises a crystallizer 1, a heat source device 4 and a second buffer tank 6. A heating medium-supply port 4c of the heat source device 4 is connected to an inlet 2a of a medium-present part 2 of the crystallizer 1, and an outlet 2b of the medium-present part 2 of the crystallizer 1 is connected to a heating medium-return port 4d of the heat source device 4. As a result, a circulation path for the heating medium is formed between the crystallizer 1 and the heat source device 4. The heating medium supplied to the medium-present part 2 of the crystallizer 1 from the heat source device 4 is heat-exchanged in the crystallizer 1, and then discharged from the medium-present part 2 of the crystallizer 1 and returned to the heat source device 4. When the heating medium is heat-exchanged in the crystallizer 1, a crystal is melted within a crystal-present part 3 of the crystallizer 1. The heating medium which has been returned to the heat source device 4 is heated by the heat source device 4 and discharged again from the heat source device 4 through the heating medium-supply port 4c.

The second buffer tank 6 is provided with an upper opening 6a connected to the heating medium-supply port 4c of the heat source device 4 and/or the outlet 2b of the medium-present part 2 of the crystallizer 1, and the heating medium-return port 4d of the heat source device 4. As a result, a path for feeding the heating medium supplied from the heat source device 4 and/or the heating medium discharged from the crystallizer 1 to the upper opening 6a of the second buffer tank 6, and a path for returning the heating medium discharged from the upper opening 6a of the second buffer tank 6 to the heat source device 4, are formed.

The second buffer tank 6 is provided with a lower opening 6b connected to the outlet 2b of the medium-present part 2 of the crystallizer 1 and the heating medium-return port 4d of the heat source device 4. As a result, a path for feeding the heating medium discharged from the crystallizer 1 to the lower opening 6b of the second buffer tank 6, and a path for returning the heating medium discharged from the lower opening 6b of the second buffer tank 6 to the heat source device 4, are formed.

According to the crystallization system of the present invention, since the crystallizer, the heat source device and the buffer tank are installed and the flow paths are formed as explained above, the heat source device works stably, crystallizing operation and/or melting operation is stabilized, and the consumption energy is reduced.

The crystallization system of the present invention may comprise two heat source devices and two buffer tanks for one crystallizer, as shown in FIG. 7.

As the heat source device, a first heat source device 4A which cools the cooling medium and a second heat source device 4B which heats the heating medium are employed. The first heat source device 4A is provided with a cooling medium-supply port 4Aa connected to the inlet of the medium-present part 2 of the crystallizer 1, and a cooling medium-return port 4Ab connected to the outlet of the medium-present part 2. The second heat source device 4B is provided with a heating medium-supply port 4Bc connected to the inlet of the medium-present part 2 of the crystallizer 1, and a heating medium-return port 4Bd connected to the outlet of the medium-present part 2. The first heat source device 4A supplies the cooling medium into the crystallizer 1, whereby crystallizing operation is performed in the crystallizer 1, and the second heat source device 4B supplies the heating medium into the crystallizer 1, whereby melting operation is performed in the crystallizer 1.

As the buffer tank, a first buffer tank 5 which maintains temperature of the cooling medium returned to the first heat source device 4A constant within a certain range, and a second buffer tank 6 which maintains temperature of the heating medium returned to the second heat source device 4B constant within a certain range, are employed. Paths connecting the first buffer tank 5, the first heat source device 4A and the crystallizer 1 are the same as FIG. 1, which represents the crystallization system where crystallizing is performed using the cooling medium. Also, paths connecting the second buffer tank 6, the second heat source device 4B and the crystallizer 1 are the same as FIG. 4, which represents the crystallization system where melting is performed using the heating medium. In FIG. 7, a path for feeding at least a part of the cooling medium to be returned to the first heat source device 4A from the crystallizer 1 into the lower part of the first buffer tank 5 is omitted, and a path for feeding at least a part of the heating medium to be returned to the second heat source device 4B from the crystallizer 1 into the upper part of the second buffer tank 6 is omitted.

The crystallization system of the present invention may comprise two crystallizers and two buffer tanks for one refrigerator. This embodiment is explained referring to FIG. 8.

As the crystallizer, a first crystallizer 1A and a second crystallizer 1B are employed. The first crystallizer 1A is provided with a first heat-transfer surface, and has a first medium-present part 2A and a first crystal-present part 3A partitioned by the first heat-transfer surface; and a second crystallizer 1B is provided with a second heat-transfer surface, and has a second medium-present part 2B and a second crystal-present part 3B partitioned by the second heat-transfer surface.

A refrigerator 7 is provided with a cooling medium-supply port 7a connected to an inlet of the first medium-present part 2A, a cooling medium-return port 7b connected to an outlet of the first medium-present part 2A, a heating medium-supply port 7c connected to an inlet of the second medium-present part 2B, and a heating medium-return port 7d connected to an outlet of the second medium-present part 2B.

As the buffer tank, a first buffer tank 5 which maintains temperature of the cooling medium returned to the refrigerator 7 constant within a certain range, and a second buffer tank 6 which maintains temperature of the heating medium returned to the refrigerator 7 constant within a certain range, are employed. Paths connecting the first buffer tank 5, the refrigerator 7 and the crystallizer 1 are the same as FIG. 1, which represents the crystallization system where crystallizing is performed using the cooling medium. Also, paths connecting the second buffer tank 6, the refrigerator 7 and the crystallizer 1 are the same as FIG. 4, which represents the crystallization system where melting is performed using the heating medium. In FIG. 8, a path for feeding at least a part of the cooling medium to be returned to the refrigerator 7 from the crystallizer 1 into the lower part of the first buffer tank 5 is omitted, and a path of feeding at least a part for the heating medium to be returned to the refrigerator 7 from the crystallizer 1 into the upper part of the second buffer tank 6 is omitted.

In the embodiment shown in FIG. 8, it is preferred that both a path 31, which connects the inlet of the medium-present part 2A of the first crystallizer 1A and the inlet of the medium-present part 2B of the second crystallizer 1B, and a path 32, which connects the outlet of the medium-present part 2A of the first crystallizer 1A and the outlet of the medium-present part 2B of the second crystallizer 1B, are provided. Each of the paths 31 and 32 has a path for the cooling medium and a path for the heating medium.

When the refrigerator is used as the heat source device, cooling of the cooling medium and heating of the heating medium can be carried out simultaneously, and hence, it becomes possible that the cooling medium is supplied to the first crystallizer 1A from the refrigerator 7, thereby conducting crystallizing operation in the first crystallizer 1A, as well as the heating medium is supplied to the second crystallizer 1B from the refrigerator 7, thereby conducting melting operation in the second crystallizer 1B. After the crystallizing operation in the first crystallizer 1A and the melting operation in the second crystallizer 1B are finished, it is preferred that the cooling medium is supplied to the second crystallizer 1B and the heating medium is supplied to the first crystallizer 1A through the path 31, while the cooling medium discharged from the second crystallizer 1B is returned to the cooling medium-return port 7b of the refrigerator 7 and the heating medium discharged from the first crystallizer 1A is returned to the heating medium-return port 7d of the refrigerator 7 through the path 32. When the crystallization system shown in FIG. 8 are used in this manner, the crystallizing operation and the melting operation can be efficiently carried out.

In the crystallization system of the present invention, a heat source device which supplies a first cooling medium and a second cooling medium whose temperature is lower than the temperature of the first cooling medium. For example, a refrigerator supplying the first cooling medium, the second cooling medium and a heating medium is used, and the crystallization system may constructed by combining three crystallizers and three buffer tanks with this refrigerator. This embodiment is explained referring to FIG. 9.

As the crystallizer, a first crystallizer 1A, a second crystallizer 1B and a third crystallizer 1C are employed. The first crystallizer 1A is provided with a first heat-transfer surface, and has a first medium-present part 2A and a first crystal-present part 3A partitioned by the first heat-transfer surface; a second crystallizer 1B is provided with a second heat-transfer surface, and has a second medium-present part 2B and a second crystal-present part 3B partitioned by the second heat-transfer surface; and a third crystallizer 1C is provided with a third heat-transfer surface, and has a third medium-present part 2C and a third crystal-present part 3C partitioned by the third heat-transfer surface.

A refrigerator 7 is provided with a first cooling medium-supply port $7a_1$ connected to an inlet of the first medium-present part 2A, a first cooling medium-return port $7b_1$ connected to an outlet of the first medium-present part 2A, a second cooling medium-supply port $7a_2$ connected to an inlet of the second medium-present part 2B, a second cooling medium-return port $7b_2$ connected to an outlet of the second medium-present part 2B, a heating medium-supply port 7c connected to an inlet of the third medium-present part 2C, and a heating medium-return port 7d connected to an outlet of the third medium-present part 2C.

As the buffer tank, a first buffer tank (1) 5A which maintains temperature of the first cooling medium returned to the refrigerator 7 constant within a certain range, a first buffer tank (2) 5B which maintains temperature of the second cooling medium returned to the refrigerator 7 constant within a certain range, and a second buffer tank 6 which maintains temperature of the heating medium returned to the refrigerator 7 constant within a certain range, are employed. Paths connecting the first buffer tanks 5A and 5B, the refrigerator 7 and the crystallizer 1 are the same as FIG. 1, which represents the crystallization system where crystallizing is performed using the cooling medium. Also, paths connecting the second buffer tank 6, the refrigerator 7 and the crystallizer 1 are the same as FIG. 4, which represents the crystallization system where melting is performed using the heating medium. In FIG. 9, paths for feeding at least a part of the cooling medium to be returned to the refrigerator 7 from the crystallizer into the lower part of the first buffer tanks 5A and 5B are omitted, and a path for feeding at least a part of the heating medium to be returned to the refrigerator 7 from the crystallizer into the upper part of the second buffer tank 6 is omitted.

In the embodiment shown in FIG. 9, it is preferred that both a path 33, which connects the inlet of the medium-present part 2A of the first crystallizer 1A, the inlet of the medium-present part 2B of the second crystallizer 1B and the inlet of the medium-present part 2C of the third crystallizer 1C, and a path 34, which connects the outlet of the medium-present part 2A of the first crystallizer 1A, the outlet of the medium-present part 2B of the second crystallizer 1B and the outlet of the medium-present part 2C of the third crystallizer 1C, are provided. Each of the paths 33 and 34 has a path for the first cooling medium, a path for the second cooling medium and a path for the heating medium.

According to the embodiment shown in FIG. 9, a solution to be crystallized is cooled by the first cooling medium, thereby conducting a former part of the crystallizing operation, and the cooled solution is crystallized by the second cooling medium, thereby conducting a latter part of the crystallizing operation. When the first cooling medium and the second cooling medium are used like the above, saving of energy in the crystallizing operation can be achieved. In the former part of the crystallizing step, a part of the solution may be crystallized when the solution is cooled by the first cooling medium.

After the former part of the crystallizing operation in the first crystallizer 1A, the latter part of the crystallizing operation in the second crystallizer 1B, and the melting operation in the third crystallizer 1C are finished, the second cooling medium is supplied to the first crystallizer 1A, the heating medium is supplied to the second crystallizer 1B, and the first cooling medium is supplied to the third crystallizer 1C through the path 33, while the second cooling medium discharged from the first crystallizer 1A is returned to the second cooling medium-return port 7b₂ of the refrigerator 7, the heating medium discharged from the second crystallizer 1B is returned to the heating medium-return port 7d of the refrigerator 7, and the first cooling medium discharged from the third crystallizer 1C is returned to the first cooling medium-return port 7b₁ of the refrigerator 7 through the path 34. As a result, the latter part of the crystallizing operation is performed in the first crystallizer 1A, the melting operation is performed in the second crystallizer 1B, and the former part of the crystallizing operation is performed in the third crystallizer 1C. Similarly, after the latter part of the crystallizing operation in the first crystallizer 1A, the melting operation in the second crystallizer 1B, and the former part of the crystallizing operation in the third crystallizer 1C are finished, the paths 33 and 34 are operated, and the melting operation is performed in the first crystallizer 1A, the former part of the crystallizing operation is performed in the second crystallizer 1B, and the latter part of the crystallizing operation is performed in the third crystallizer 1C. When the crystallization system shown in FIG. 9 are used in this manner, the crystallizing operation and the melting operation can be efficiently carried out and the consumption energy of the crystallizer 7 can be further decreased.

EXAMPLES (1) Effect of Using a Buffer Tank
(1-1) In the Case of Using a Buffer Tank Purified acrylic acid was produced from a crude acrylic acid solution using a crystallization system shown in FIG. 9. As a heat source device, an absorption refrigerator was employed. From the absorption refrigerator, a first cooling medium having temperature of 0° C., a second cooling medium having temperature of −30° C. and a heating medium having temperature of 40° C. are respectively discharged at flow rates of 300 m³/h. Concerning a crystallizer, a crystallizer provided with a heat-transfer surface and having a medium-present part and a crystal-present part partitioned by the heat-transfer surface was used.

The crude acrylic acid solution consisted of 94.3 mass % of acrylic acid, 2.3 mass % of water, 2.0 mass % of acetic acid, 0.4 mass % of maleic acid, and 1.0 mass % of other impurities. 20 ton of the crude acrylic acid solution of 30° C. was supplied to the crystal-present part of the crystallizer while the first cooling medium of 0° C. was supplied to the medium-present part of the crystallizer, thereby conducting a former part of the crystallizing step. On this occasion, a first buffer tank (1) which retains a certain amount of the first cooling medium was utilized so that the temperature of the first cooling medium returned to the refrigerator was maintained at 5° C.

The temperature of the first cooling medium returned to the refrigerator was monitored, and when the temperature exceeded 5° C., a part of the first cooling medium discharged from the crystallizer was fed to an upper part of the first buffer tank (1) and the first cooling medium was discharged from a lower part of the first buffer tank (1) in equal amount. The first cooling medium discharged from the lower part of the first buffer tank (1) was returned to the refrigerator along with the rest of the first cooling medium discharged from the crystallizer. On this occasion, the first cooling medium was fed to the first buffer tank (1) at 150 m³/h to 300 m³/h and returned to the refrigerator without flowing through the first buffer tank (1) at 0 m³/h to 150 m³/h.

When the temperature of the first cooling medium returned to the refrigerator fell below 5° C., a part of the first cooling medium of 0° C., that is to be supplied to the crystallizer from the refrigerator, was fed to the lower part of the first buffer tank (1) and the first cooling medium was discharged from the upper part of the first buffer tank (1) in equal amount. The first cooling medium discharged from the upper part of the first buffer tank (1) was returned to the refrigerator along with the first cooling medium discharged from the crystallizer. On this occasion, the first cooling medium was fed to the crystallizer at 150 m³/h to 300 m³/h and fed to the first buffer tank (1) at 0 m³/h to 150 m³/h.

The former part of the crystallizing step was conducted for 40 minutes, and refrigerating performance of the refrigerator was 1250 kW during this operation.

Subsequently, the second cooling medium of −30° C. was supplied to the medium-present part of the crystallizer, thereby conducting a latter part of the crystallizing step. On this occasion, a first buffer tank (2) which retains a certain amount of the second cooling medium was utilized so that the temperature of the second cooling medium returned to the refrigerator was maintained at −25° C.

The temperature of the second cooling medium returned to the refrigerator was monitored, and depending on the cases whether the temperature exceeded −25° C. or fell below −25° C., the first buffer tank (2) was utilized in the same manner as the case of the first cooling medium. The latter part of the crystallizing step was conducted for 40 minutes, resulting in obtaining an acrylic acid crystal. The refrigerating performance of the refrigerator was 1250 kW in the latter part of the crystallizing step.

Subsequently, the heating medium of 40° C. was supplied to the medium-present part of the crystallizer, thereby conducting the melting step. In the melting step, a sweating operation was also conducted. On this occasion, a second buffer tank which retains a certain amount of the heating medium was utilized so that the temperature of the heating medium returned to the refrigerator was maintained at 35° C.

The temperature of the heating medium returned to the refrigerator was monitored, and when the temperature fell below 35° C., a part of the heating medium discharged from the crystallizer was fed to a lower part of the second buffer tank and the heating medium was discharged from an upper part of the second buffer tank in equal amount. The heating medium discharged from the upper part of the second buffer tank was returned to the refrigerator along with the rest of the heating medium discharged from the crystallizer. On this occasion, the heating medium was fed to the second buffer tank at 150 m$^3$/h to 300 m$^3$/h and returned to the refrigerator without flowing through the second buffer tank at 0 m$^3$/h to 150 m$^3$/h.

When the temperature of the heating medium returned to the refrigerator exceeded 35° C., a part of the heating medium at 40° C., that is to be supplied to the crystallizer from the refrigerator, was fed to the upper part of the second buffer tank and the heating medium was discharged from the lower part of the second buffer tank in equal amount. The heating medium discharged from the lower part of the second buffer tank was returned to the refrigerator along with the heating medium discharged from the crystallizer. On this occasion, the heating medium was fed to the crystallizer at 150 m$^3$/h to 300 m$^3$/h and fed to the second buffer tank at 0 m$^3$/h to 300 m$^3$/h.

The melting step was conducted for 40 minutes, resulting in obtaining 15 ton of an acrylic acid melt, that is, the purified acrylic acid. The refrigerating performance of the refrigerator was −2500 kW in the melting step. Here, the refrigerating performance means "an amount of heat acquired from an object per unit time", and the performance for cooling was represented by "+" and the performance for heating was represented by "−".

(1-2) In the Case of Using a Buffer Tank not According to the Operations of the Present Invention The former and latter parts of the crystallizing step and the melting step were conducted in the same manner as in the Example of the above section (1-1), except that the first cooling medium, the second cooling medium and the heating medium discharged from the crystallizer were wholly fed to corresponding buffer tanks and continuously returned to the refrigerator from the buffer tanks. The temperature of each of the first cooling medium, the second cooling medium and the heating medium returned to the refrigerator was changed in the range of about 10° C. in each step. As a result, the refrigerator could not work stably while maintaining the temperature of the each medium supplied to the crystallizer from the refrigerator constant, whereby the crystallization operation was destabilized and the energy consumption was increased.

(1-3) In the Case of not Using a Buffer Tank

The former and latter parts of the crystallizing step and the melting step were conducted in the same manner as in the Example of the above section (1-1), except that the buffer tank was not used. The temperature range of each of the first cooling medium, the second cooling medium and the heating medium returned to the refrigerator was more than 20° C. in each step, and the refrigerator could not work so as to maintain the temperature of the each medium supplied to the crystallizer from the refrigerator constant, whereby the crystallization operation was destabilized and the energy consumption was increased.

(2) Effect of Utilizing a Cooling Medium and a Heating Medium as the Mutual Sources (2-1) In the Case of Mutually-Utilizing a Cooling Medium and a Heating Medium Purified acrylic acid was produced from a crude acrylic acid solution using a crystallization system shown in FIG. 9, in the same manner as in the Example of the above section (1-1). The buffer tank was not used in the production of the purified acrylic acid. The crude acrylic acid solution used was the same as that in the Example of the above section (1-1). The temperatures and the amounts of the respective mediums discharged from the crystallizer were the same as those in the Example of the above section (1-1).

20 ton of the crude acrylic acid solution of 30° C. was supplied to the crystal-present part of a first crystallizer while the first cooling medium of 0° C. was supplied to the medium-present part of the first crystallizer, thereby conducting a former part of the crystallizing step. In the first crystallizer, prior to the former part of the crystallizing step, the melting step was conducted.

While the former part of the crystallizing step was conducted in the first crystallizer, the latter part of the crystallizing step and the melting step were conducted in a second crystallizer and a third crystallizer, respectively. In the crystal-present part of the second crystallizer, a cooled crude acrylic acid solution, which had been obtained by conducting the former part of the crystallizing step, was present, and the latter part of the crystallizing step was conducted by supplying the second cooling medium of −30° C. into the medium-present part of the second crystallizer. In the crystal-present part of the third crystallizer, crystallized acrylic acid, which had been formed by conducting the latter part of the crystallizing step, was present, and the melting step was conducted by supplying the heating medium into the medium-present part of the third crystallizer. As a result, 15 ton of an acrylic acid melt, that is, the purified acrylic acid, was obtained. In the melting step, a sweating operation was also conducted.

Into the first crystallizer, the first cooling medium of 0° C. was supplied, and the first cooling medium discharged from the first crystallizer was utilized as a source of the heating medium at the moment soon after the start of the former part of the crystallizing step, since the first cooling medium discharged from the first crystallizer had temperature of 20° C. or higher. The first cooling medium discharged from the first crystallizer was utilized as the source of the heating medium until the temperature of that fell below 20° C., that temperature corresponded to the average of temperatures of the first cooling medium and the heating medium discharged from the refrigerator, and after the temperature of the first cooling medium discharged from the first crystallizer fell below 20° C., the first cooling medium was utilized as a source of the first cooling medium.

Into the second crystallizer, the second cooling medium of −30° C. was supplied, and the second cooling medium discharged from the second crystallizer was utilized as a source of the first cooling medium at the moment soon after the start of the latter part of the crystallizing step, since the second cooling medium discharged from the second crystallizer had temperature of −15° C. or higher. The second cooling medium discharged from the second crystallizer was utilized as the source of the first cooling medium until the temperature of that fell below −15° C., that temperature corresponded to the average of temperatures of the second cooling medium and the first cooling medium discharged from the refrigerator, and after the temperature of the second cooling medium discharged from the second crystallizer fell below −15° C., the second cooling medium was utilized as a source of the second cooling medium.

Into the third crystallizer, the heating medium of 40° C. was supplied, and the heating medium discharged from the third crystallizer was utilized as a source of the second cooling medium at the moment soon after the start of the melting step, since the heating medium discharged from the third crystallizer had temperature of 5° C. or lower. The heating medium discharged from the third crystallizer was utilized as the source of the second cooling medium until the temperature of that exceeded 5° C., that temperature corresponded to the average of temperatures of the heating medium and the second cooling medium discharged from the refrigerator, and after the temperature of the heating medium discharged from the third crystallizer exceeded 5° C., the heating medium was utilized as a source of the heating medium.

The respective steps were conducted for 40 minutes. The mean electric power of the refrigerator in the each step was as follows: refrigerating performance for cooling the first cooling medium to 0° C. was 1100 kW; refrigerating performance for cooling the second cooling medium to −30° C. was 1100 kW; and refrigerating performance for heating the heating medium to 40° C. was −2250 kW. Here, the refrigerating performance means "an amount of heat acquired from an object per unit time". Thus, the performance for cooling was represented by "+" and the performance for heating was represented by "−".

(2-2) In the Case of not Mutually-Utilizing a Cooling Medium and a Heating Medium The former part of the crystallizing step, the latter part of the crystallizing step and the melting step were conducted in the respective crystallizer in the same manner as in the Example of the above section (2-1), except that the first cooling medium was utilized wholly to the source of the first cooling medium, the second cooling medium was utilized wholly to the source of the second cooling medium, and the heating medium was utilized wholly to the source of the heating medium.

The mean electric power of the refrigerator in the each step was as follows: refrigerating performance for cooling the first cooling medium to 0° C. was 1225 kW; refrigerating performance for cooling the second cooling medium to −30° C. was 1225 kW; and refrigerating performance for heating the heating medium to 40° C. was −2500 kW.

INDUSTRIAL APPLICABILITY

The present invention can be used for a process for producing (meth)acrylic acid comprising a crystallizing step and/or a melting step. Also, the crystallization system of the present invention can be used for crystallizing and/or melting.

EXPLANATION OF REFERENCE 1, 1A, 1B, 1C: crystallizer
4, 4A, 4B: heat source device
5, 5A, 5B: first buffer tank
6: second buffer tank
7: refrigerator

The invention claimed is:
1. A process for producing (meth)acrylic acid, comprising the steps of:
supplying a cooling medium to a crystallizer from a heat source device, thereby crystallizing (meth)acrylic acid from a crude (meth)acrylic acid solution; and
discharging the cooling medium from the crystallizer and returning the cooling medium to the heat source device;
wherein:
temperature of the cooling medium returned to the heat source device is maintained constant by a first adjustment operation or a second adjustment operation;
the first adjustment operation is performed by feeding at least a part of the cooling medium to be returned to the heat source device from the crystallizer into an upper part of a first buffer tank and discharging the cooling medium from a lower part of the first buffer tank to return to the heat source device; and
the second adjustment operation is performed by feeding at least a part of the cooling medium to be supplied to the crystallizer from the heat source device and/or the cooling medium to be returned to the heat source device from the crystallizer into the lower part of the first buffer tank and discharging the cooling medium from the upper part of the first buffer tank to return to the heat source device.

2. A process for producing (meth)acrylic acid, comprising the steps of:
supplying a heating medium to a crystallizer from a heat source device, thereby melting crystallized (meth)acrylic acid; and
discharging the heating medium from the crystallizer and returning the heating medium to the heat source device;
wherein:
temperature of the heating medium returned to the heat source device is maintained constant by a third adjustment operation or a fourth adjustment operation;
the third adjustment operation is performed by feeding at least a part of the heating medium to be returned to the heat source device from the crystallizer into an lower part of a second buffer tank and discharging the heating medium from an upper part of the second buffer tank to return to the heat source device; and
the fourth adjustment operation is performed by feeding at least a part of the heating medium to be supplied to the crystallizer from the heat source device and/or the heating medium to be returned to the heat source device from the crystallizer into the upper part of the second buffer tank and discharging the heating medium from the lower part of the second buffer tank to return to the heat source device.

3. A process for producing (meth)acrylic acid, comprising the steps of:
supplying a cooling medium to a crystallizer from a heat source device, thereby crystallizing (meth)acrylic acid from a crude (meth)acrylic acid solution;
discharging the cooling medium from the crystallizer and returning the cooling medium to the heat source device;
supplying a heating medium to the crystallizer from a heat source device, thereby melting the (meth)acrylic acid; and
discharging the heating medium from the crystallizer and returning the heating medium to the heat source device;
wherein:
temperature of the cooling medium returned to the heat source device is maintained constant by a first adjustment operation or a second adjustment operation;

temperature of the heating medium returned to the heat source device is maintained constant by a third adjustment operation or a fourth adjustment operation;

the first adjustment operation is performed by feeding at least a part of the cooling medium to be returned to the heat source device from the crystallizer into an upper part of a first buffer tank and discharging the cooling medium from a lower part of the first buffer tank to return to the heat source device;

the second adjustment operation is performed by feeding at least a part of the cooling medium to be supplied to the crystallizer from the heat source device and/or the cooling medium to be returned to the heat source device from the crystallizer into the lower part of the first buffer tank and discharging the cooling medium from the upper part of the first buffer tank to return to the heat source device;

the third adjustment operation is performed by feeding at least a part of the heating medium to be returned to the heat source device from the crystallizer into an lower part of a second buffer tank and discharging the heating medium from an upper part of the second buffer tank to return to the heat source device; and the fourth adjustment operation is performed by feeding at least a part of the heating medium to be supplied to the crystallizer from the heat source device and/or the heating medium to be returned to the heat source device from the crystallizer into the upper part of the second buffer tank and discharging the heating medium from the lower part of the second buffer tank to return to the heat source device.

4. A process for producing (meth)acrylic acid, comprising the steps of:

supplying a cooling medium to a first crystallizer from a heat source device, thereby crystallizing (meth)acrylic acid from a crude (meth)acrylic acid solution;

discharging the cooling medium from the first crystallizer and returning the cooling medium to the heat source device;

supplying a heating medium to a second crystallizer from the heat source device, thereby melting crystallized (meth)acrylic acid; and discharging the heating medium from the second crystallizer and returning the heating medium to the heat source device;

wherein:

the heat source device is a refrigerator;

temperature of the cooling medium returned to the heat source device is maintained constant by a first adjustment operation or a second adjustment operation;

temperature of the heating medium returned to the heat source device is maintained constant by a third adjustment operation or a fourth adjustment operation;

the first adjustment operation is performed by feeding at least a part of the cooling medium to be returned to the heat source device from the first crystallizer into an upper part of a first buffer tank and discharging the cooling medium from a lower part of the first buffer tank to return to the heat source device;

the second adjustment operation is performed by feeding at least a part of the cooling medium to be supplied to the first crystallizer from the heat source device and/or the cooling medium to be returned to the heat source device from the first crystallizer into the lower part of the first buffer tank and discharging the cooling medium from the upper part of the first buffer tank to return to the heat source device;

the third adjustment operation is performed by feeding at least a part of the heating medium to be returned to the heat source device from the second crystallizer into an lower part of a second buffer tank and discharging the heating medium from an upper part of the second buffer tank to return to the heat source device; and the fourth adjustment operation is performed by feeding at least a part of the heating medium to be supplied to the second crystallizer from the heat source device and/or the heating medium to be returned to the heat source device from the second crystallizer into the upper part of the second buffer tank and discharging the heating medium from the lower part of the second buffer tank to return to the heat source device.

5. The process for producing (meth)acrylic acid according to claim 4, wherein a part or all of the cooling medium discharged from the first crystallizer is utilized as a source of the heating medium, and a part or all of the heating medium discharged from the second crystallizer is utilized as a source of the cooling medium.

6. The process for producing (meth)acrylic acid according to claim 5, wherein the cooling medium discharged from the first crystallizer is utilized as the source of the heating medium when temperature of the cooling medium discharged from the first crystallizer is higher than that of the heating medium discharged from the second crystallizer; and the heating medium discharged from the second crystallizer is utilized as the source of the cooling medium when temperature of the heating medium discharged from the second crystallizer is lower than that of the cooling medium discharged from the first crystallizer.

7. The process for producing (meth) acrylic acid according to claim 5, wherein the cooling medium discharged from the first crystallizer is utilized as the source of the heating medium when temperature of the cooling medium discharged from the first crystallizer is higher than a predetermined temperature between temperature of the cooling medium supplied from the heat source device and temperature of the heating medium supplied from the heat source device; and the heating medium discharged from the second crystallizer is utilized as the source of the cooling medium when temperature of the heating medium discharged from the second crystallizer is lower than the predetermined temperature between temperature of the cooling medium supplied from the heat source device and temperature of the heating medium supplied from the heat source device.

8. The process for producing (meth)acrylic acid according to claim 3, wherein the first buffer tank retains a certain amount of the cooling medium, the second buffer tank retains a certain amount of the heating medium, and each of the cooling medium retained in the first buffer tank and the heating medium retained in the second buffer tank has a temperature gradient such that an upper part is high-temperature and a lower part is low-temperature.

9. The process for producing (meth)acrylic acid according to claim 8, wherein temperature of the cooling medium returned to the heat source device is adjusted depending on temperatures of the upper part and the lower part of the cooling medium retained in the first buffer tank, and temperature of the heating medium returned to the heat source device is adjusted depending on temperatures of the upper part and the lower part of the heating medium retained in the second buffer tank.

10. The process for producing (meth)acrylic acid according to claim 3, wherein
the first buffer tank is provided with openings at an upper part and a lower part thereof, through which the cooling medium passes, wherein distance between the opening at the upper part and the opening at the lower part of the first buffer tank is equal to or more than a maximum cross-section length of the first buffer tank, and
the second buffer tank is provided with openings at an upper part and a lower part thereof, through which the heating medium passes, wherein distance between the opening at the upper part and the opening at the lower part of the second buffer tank is equal to or more than a maximum cross-section length of the second buffer tank.

11. The process for producing (meth)acrylic acid according to claim 1, further comprising the steps of:
dehydrating glycerin or 2-methylglycerin to convert to (meth)acrolein; and
oxidizing the (meth)acrolein to convert to (meth)acrylic acid, thereby obtaining the crude (meth)acrylic acid solution.

12. The process for producing (meth)acrylic acid according to claim 1, further comprising the step of:
dehydrating hydroxypropionic acid or 2-methyl-3-hydroxypropionic acid to convert to (meth)acrylic acid, thereby obtaining the crude (meth)acrylic acid solution.

13. A process for producing a hydrophilic resin, comprising the step of:
polymerizing a monomeric component(s) including the (meth)acrylic acid obtained by the producing process according to claim 1.

14. A process for producing an absorbent resin, comprising the step of:
polymerizing a monomeric component(s) including the (meth)acrylic acid obtained by the producing process according to claim 1.

15. The process for producing (meth)acrylic acid according to claim 1, wherein
the first buffer tank retains a certain amount of the cooling medium, and
the cooling medium retained in the first buffer tank has a temperature gradient such that an upper part is high-temperature and a lower part is low-temperature.

16. The process for producing (meth)acrylic acid according to claim 15, wherein
temperature of the cooling medium returned to the heat source device is adjusted depending on temperatures of the upper part and the lower part of the cooling medium retained in the first buffer tank.

17. The process for producing (meth)acrylic acid according to claim 1, wherein
the first buffer tank is provided with openings at an upper part and a lower part thereof, through which the cooling medium passes, wherein distance between the opening at the upper part and the opening at the lower part of the first buffer tank is equal to or more than a maximum cross-section length of the first buffer tank.

18. The process for producing (meth)acrylic acid according to claim 2, wherein
the second buffer tank retains a certain amount of the heating medium, and
the heating medium retained in the second buffer tank has a temperature gradient such that an upper part is high-temperature and a lower part is low-temperature.

19. The process for producing (meth)acrylic acid according to claim 18, wherein
temperature of the heating medium returned to the heat source device is adjusted depending on temperatures of the upper part and the lower part of the heating medium retained in the second buffer tank.

20. The process for producing (meth)acrylic acid according to claim 2, wherein
the second buffer tank is provided with openings at an upper part and a lower part thereof, through which the heating medium passes, wherein distance between the opening at the upper part and the opening at the lower part of the second buffer tank is equal to or more than a maximum cross-section length of the second buffer tank.

* * * * *